US012782330B2

(12) United States Patent
Niinomi et al.

(10) Patent No.: US 12,782,330 B2
(45) Date of Patent: Nov. 3, 2026

(54) AIR QUALITY DETERMINATION SYSTEM, AIR QUALITY DETERMINATION METHOD, AND SENSOR MODULE

(71) Applicant: PANASONIC HOUSING SOLUTIONS CO., LTD., Osaka (JP)

(72) Inventors: Toshiki Niinomi, Osaka (JP); Atsuo Nakao, Nara (JP); Yosuke Hanai, Osaka (JP); Takahiro Nogami, Osaka (JP)

(73) Assignee: PANASONIC HOUSING SOLUTIONS CO., LTD., Osaka (JP)

(*) Notice: Subject to any disclaimer, the term of this patent is extended or adjusted under 35 U.S.C. 154(b) by 683 days.

(21) Appl. No.: 18/253,342

(22) PCT Filed: Nov. 26, 2021

(86) PCT No.: PCT/JP2021/043503
§ 371 (c)(1),
(2) Date: May 17, 2023

(87) PCT Pub. No.: WO2022/114158
PCT Pub. Date: Jun. 2, 2022

(65) Prior Publication Data
US 2024/0036018 A1 Feb. 1, 2024

(30) Foreign Application Priority Data
Nov. 30, 2020 (JP) ................................ 2020-199098

(51) Int. Cl.
*G01N 33/00* (2006.01)
*G01N 1/22* (2006.01)
*G01N 27/14* (2006.01)

(52) U.S. Cl.
CPC ....... *G01N 33/0016* (2013.01); *G01N 1/2273* (2013.01); *G01N 27/14* (2013.01); *G01N 33/0047* (2013.01)

(58) Field of Classification Search
CPC .. G01N 33/0016; G01N 1/2273; G01N 27/14; G01N 33/0047; G01N 33/0031; G01N 33/0034
See application file for complete search history.

(56) References Cited

U.S. PATENT DOCUMENTS

2005/0263394 A1* 12/2005 Lewis ................ G01N 33/0031 204/403.01
2007/0095678 A1 5/2007 West et al.
2018/0017536 A1* 1/2018 Le Neel ............. G01N 33/0047

FOREIGN PATENT DOCUMENTS

JP S52-138196 A 11/1977
JP H04-218759 A 8/1992
(Continued)

OTHER PUBLICATIONS

Yasuhiro Matsubara, "Study on Intelligent Gas Sensing Using Information Analysis for Dynamic Response of Gas Sensing System Consisted of TGS-825 Gas Sensor Element Which Performed with Sinusoidal Changes of Its Surface Temperature.", Memoirs of Niihama National College of Technology, 2017, vol. 54, p. 53-58, with English Translation.
(Continued)

*Primary Examiner* — David Z Huang
(74) *Attorney, Agent, or Firm* — Rimon P.C.

(57) ABSTRACT

An air quality determination method including a temperature control step, an acquisition step, a determination step, and an output step. The temperature control step includes controlling a temperature of a sensitive unit exposed to a sample gas to cause the temperature of the sensitive unit to vary in a temperature variation pattern including at least one tempera-
(Continued)

ture rising period in which the temperature of the sensitive unit rises and at least one temperature falling period in which the temperature of the sensitive unit falls. The acquisition step includes acquiring an electrical characteristic value of the sensitive unit exposed to the sample gas. The determination step includes determining, using a learned model to determine an air quality condition of the sample gas, the air quality condition of the sample gas based on a variation in the electrical characteristic value. The output step includes outputting a decision made in the determination step.

20 Claims, 19 Drawing Sheets

(56) References Cited

FOREIGN PATENT DOCUMENTS

| | | | |
|---|---|---|---|
| JP | H06-130017 | A | 5/1994 |
| JP | H06-148116 | A | 5/1994 |
| JP | 2001-021513 | A | 1/2001 |
| JP | 2001-296265 | A | 10/2001 |
| JP | 2004-233158 | A | 8/2004 |
| JP | 2018-105659 | A | 7/2018 |

OTHER PUBLICATIONS

International Search Report dated Jan. 11, 2022 issued in International Patent Application No. PCT/JP2021/043503, with English translation.

Office Action issued for the corresponding Chinese Patent Application No. 202180076371.6, dated Apr. 20, 2026.

* cited by examiner

AIR QUALITY DETERMINATION SYSTEM, AIR QUALITY DETERMINATION METHOD, AND SENSOR MODULE

CROSS-REFERENCE OF RELATED APPLICATIONS

This application is the U.S. National Phase under 35 U.S.C. § 371 of International Patent Application No. PCT/JP2021/043503, filed on Nov. 26, 2021, which in turn claims the benefit of Japanese Patent Application No. 2020-199098, filed on Nov. 30, 2020, the entire disclosures of which Applications are incorporated by reference herein.

TECHNICAL FIELD

The present disclosure generally relates to an air quality determination system, an air quality determination method, and a sensor module. More particularly, the present disclosure relates to an air quality determination system, an air quality determination method, and a sensor module, all of which are configured or designed to determine an air quality condition of a sample gas.

BACKGROUND ART

Patent Literature 1 discloses a gas detector including a semiconductor gas detecting element, an electrical heating control unit, and a calculating unit. The electrical heating control unit alternately and repeatedly exhibits a first energized state in which the gas detecting element is purge heated with voltage applied thereto and a second energized state in which an atmospheric gas is adsorbed into the gas detecting element to maintain the gas detecting element in an adsorbed state. The calculating unit calculates the difference between a first output of the gas detecting element right after a transition has been made from the first energized state to the second energized state and a second output of the gas detecting element at an end point of the second energized state and determines, based on this difference, whether an alarm should be sounded.

In the gas detector, the output of the gas detecting element has temperature dependence, and therefore, in the second energized state in which the temperature is lower than in the first energized state, the second output may include some variation components caused by the environmental temperature. In that case, the difference between the first output and the second output may vary according to the environmental temperature, thus possibly causing the air quality condition of a sample gas to be determined erroneously.

CITATION LIST

Patent Literature

Patent Literature 1: JP 2001-296265 A

SUMMARY OF INVENTION

It is therefore an object of the present disclosure to provide an air quality determination system, an air quality determination method, and a sensor module having the ability to reduce the chances of causing a decline in the accuracy of the air quality condition determined.

An air quality determination method according to an aspect of the present disclosure is a method for determining an air quality using a sensitive unit, of which an electrical characteristic value changes in reaction to one or more types of molecules. The air quality determination method includes a temperature control step, an acquisition step, a determination step, and an output step. The temperature control step includes controlling a temperature of the sensitive unit exposed to a sample gas in a predetermined measurement period to cause the temperature of the sensitive unit to vary in a temperature variation pattern including at least one temperature rising period in which the temperature of the sensitive unit rises and at least one temperature falling period in which the temperature of the sensitive unit falls. The acquisition step includes acquiring the electrical characteristic value of the sensitive unit exposed to the sample gas. The determination step includes determining, using a learned model to determine an air quality condition of the sample gas, the air quality condition of the sample gas based on a variation in the electrical characteristic value. The output step includes outputting a decision made in the determination step.

An air quality determination method according to another aspect of the present disclosure is a method for determining an air quality using a sensitive unit, of which an electrical characteristic value changes in reaction to one or more types of molecules. The air quality determination method includes a temperature control step, an acquisition step, a determination step, and an output step. The sensitive unit includes a plurality of sensitive modules. The temperature control step includes controlling temperatures of the plurality of sensitive modules exposed to a sample gas in a predetermined measurement period to cause the temperature of each of the plurality of sensitive modules to vary in a temperature variation pattern including at least one temperature rising period in which the temperature of the sensitive module rises and at least one temperature falling period in which the temperature of the sensitive module falls. The acquisition step includes acquiring the electrical characteristic value of each of the plurality of sensitive modules exposed to the sample gas. The determination step includes determining, using a learned model to determine an air quality condition of the sample gas, the air quality condition of the sample gas based on a variation in the electrical characteristic value of each of the plurality of sensitive modules. The output step includes outputting a decision made in the determination step.

An air quality determination system according to still another aspect of the present disclosure includes a sensitive unit, an exposure unit, a temperature control element, a controller, an acquirer, a determiner, and an outputter. An electrical characteristic value of the sensitive unit changes in reaction to one or more types of molecules. The exposure unit exposes the sensitive unit to a sample gas in a predetermined measurement period. The temperature control element heats and/or cools the sensitive unit. The controller controls the temperature control element to cause a temperature of the sensitive unit exposed to the sample gas in the predetermined measurement period to vary in a temperature variation pattern including at least one temperature rising period in which the temperature of the sensitive unit rises and at least one temperature falling period in which the temperature of the sensitive unit falls. The acquirer acquires the electrical characteristic value of the sensitive unit in the predetermined measurement period. The determiner determines, using a learned model to determine an air quality condition of the sample gas, the air quality condition of the sample gas based on a variation in the electrical characteristic value. The outputter outputs a decision made by the determiner.

An air quality determination system according to yet another aspect of the present disclosure includes a plurality of sensitive modules, an exposure unit, a temperature control element, a controller, an acquirer, a determiner, and an outputter. An electrical characteristic value of each of the plurality of sensitive modules changes in reaction to one or more types of molecules. The exposure unit exposes the plurality of sensitive modules to a sample gas in a predetermined measurement period. The temperature control element heats and/or cools the plurality of sensitive modules. The controller controls the temperature control element to cause a temperature of each of the plurality of sensitive modules exposed to the sample gas in the predetermined measurement period to vary in a temperature variation pattern including at least one temperature rising period in which the temperature of the sensitive module rises and at least one temperature falling period in which the temperature of the sensitive module falls. The acquirer acquires the electrical characteristic values of the plurality of sensitive modules in the predetermined measurement period. The determiner determines, using a learned model to determine an air quality condition of the sample gas, the air quality condition of the sample gas based on variations in the electrical characteristic values of the plurality of sensitive modules. The outputter outputs a decision made by the determiner.

A sensor module according to yet another aspect of the present disclosure includes a sensitive unit and a temperature control element. An electrical characteristic value of the sensitive unit changes in reaction to one or more types of molecules. The temperature control element heats and/or cools the sensitive unit. The temperature control element causes a temperature of the sensitive unit exposed to a sample gas in a predetermined measurement period to vary in a temperature variation pattern including at least one temperature rising period in which the temperature of the sensitive unit rises and at least one temperature falling period in which the temperature of the sensitive unit falls.

DESCRIPTION OF EMBODIMENTS

An embodiment of the present disclosure will now be described with reference to the accompanying drawings as needed. Note that the embodiment to be described below is only an exemplary one of various embodiments of the present disclosure and should not be construed as limiting. The relative positions of respective constituent elements in upward, downward, rightward, and leftward directions are supposed to be defined as shown on the drawings unless otherwise stated. The drawings to be referred to in the following description of embodiments are all schematic representations. Thus, the ratio of the dimensions (including thicknesses) of respective constituent elements illustrated on the drawings does not always reflect their actual dimensional ratio. Also, the dimensional ratio of the respective elements is not limited to the ratio shown on the drawings.

As for each of the materials exemplified in the following description, the material may be used by itself or may also be used in combination with at least one more of the materials, whichever is appropriate. As for the content of each component included in a composition, if there are multiple substances corresponding to that component in the composition, the content of the component means the total content of those substances included in the composition.

EMBODIMENT

(1) Overview

Figure 1:
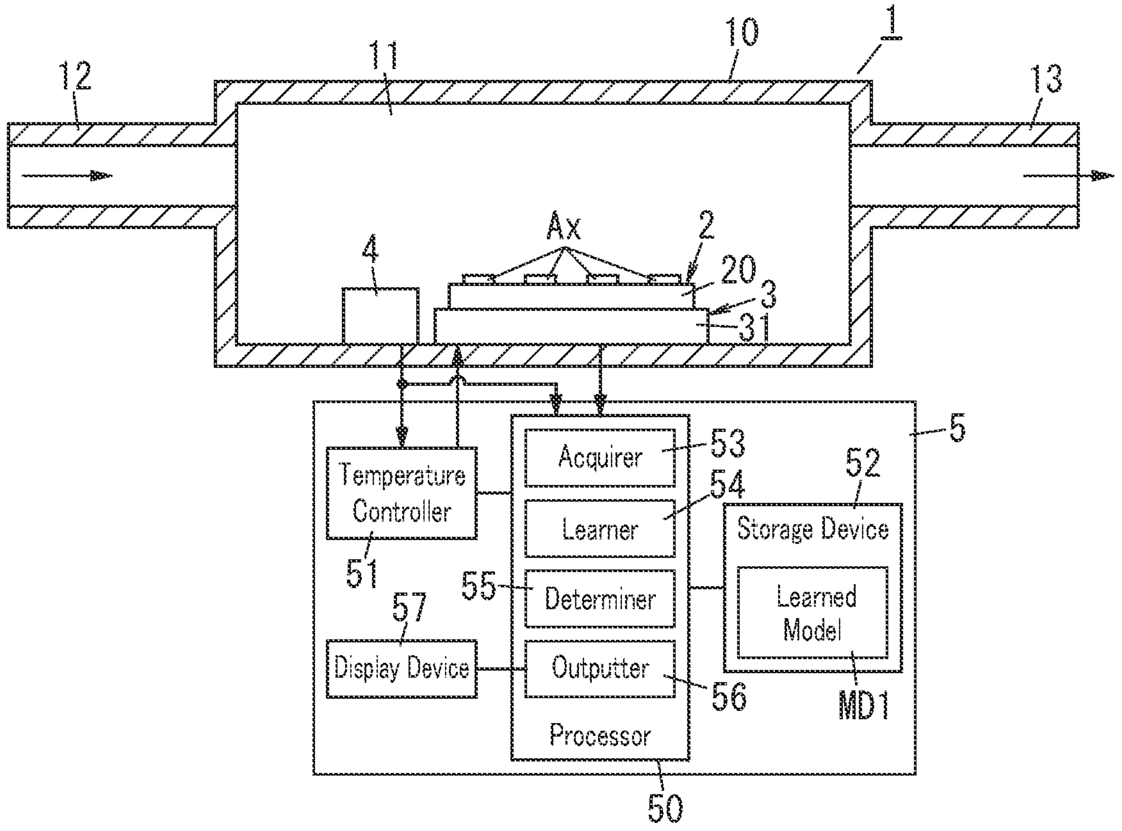
FIG. 1 illustrates a schematic system configuration for an air quality determination system according to an exemplary embodiment of the present disclosure.

FIG. 1 illustrates a schematic system configuration for an air quality determination system 1 according to an exemplary embodiment.

The air quality determination system 1 may be used to, for example, detect an odor molecule as a molecule to detect. Examples of the odor molecules to detect include volatile organic compounds (VOCs) such as benzaldehyde, nonanal, and pyrrole, which may be included in human body odor components and ammonia.

The air quality determination system 1 detects VOCs as odor molecules included in a sample gas such as a gas or a breath, including a body odor, taken from a subject's body or the air taken from a building room. Note that the molecules to be detected by the air quality determination system 1 do not have to be VOCs but may also be multiple types of odor molecules including VOCs.

The air quality determination system 1 may be used, for example, to check the subject's health condition by using, as a sample gas, the gas or breath including the body odor taken from the subject's body and determining the air quality condition of the sample gas. If the subject is the driver of a vehicle such as an automobile, a railway train, an aircraft, or a watercraft, the air quality determination system 1 may be used to check the driver's degree of fatigue or degree of arousal by determining the air quality condition of the sample gas. Alternatively, the air quality determination system 1 may also be used to make biometric authentication by determining the air quality condition of a sample gas taken from the subject. Still alternatively, the air quality determination system 1 may also be used to search for a rescuee by detecting a gas or breath, including the body odor, exhaled from the rescuee lying under the rubble at a disaster site, for example. Note that the sample gas does not have to be a gas (such as breath) exhaled from a human body. Alternatively, the air quality determination system 1 may also be used to make quality control of a food by determining whether the food emits any gas indicating its putrefaction. Still alternatively, the air quality determination system 1 may also be used to determine the air quality condition inside a room by determining whether VOCs are emitted from a building material of the room. Yet alternatively, the air quality determination system 1 may also be used to determine whether there is any gas produced by a fire, any gas emitted from an explosive or a drug, or any poisonous gas.

As shown in FIG. 1, the air quality determination system 1 includes a sensitive unit 2, an exposure unit (sensor housing chamber 10), a temperature control element 3, and a determination module 5. The determination module 5 includes at least a temperature controller 51 and a determiner 55. That is to say, the air quality determination system 1 includes the sensitive unit 2, the exposure unit (sensor housing chamber 10), the temperature control element 3, the temperature controller 51, and the determiner 55.

Figure 3:
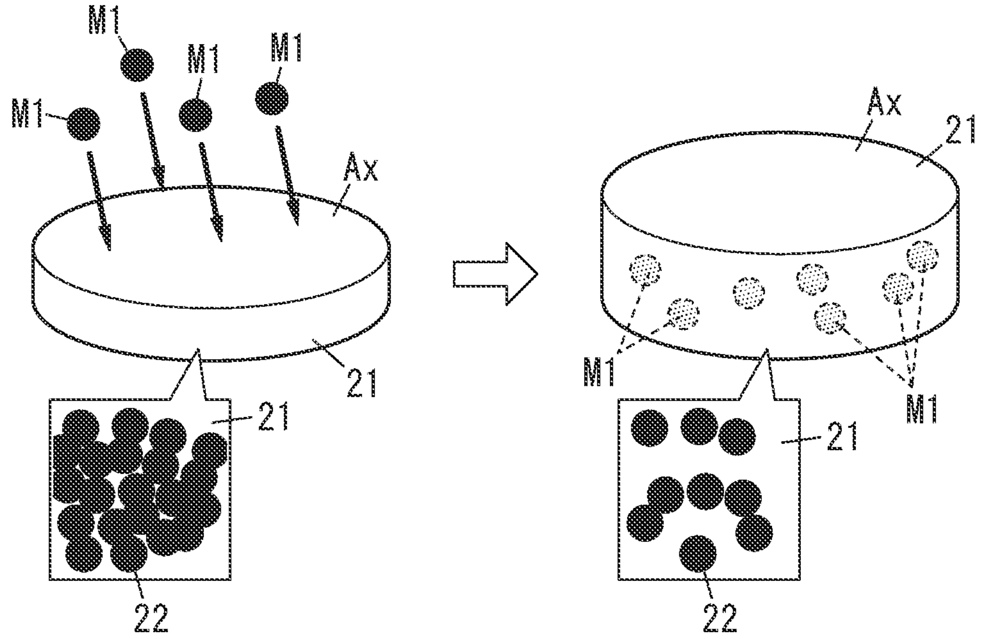
FIG. 3 schematically illustrates a state of the sensitive unit before the sensitive unit absorbs molecules to detect and a state of the sensitive unit after the sensitive unit has absorbed the molecules to detect.

As shown in FIG. 3, the sensitive unit 2 includes an organic composition 21 and conductive particles 22 dispersed in the organic composition 21. An electrical characteristic value of the sensitive unit 2 changes in reaction to one or more types of molecules to which the sensitive unit 2 is sensitive.

The exposure unit (sensor housing chamber 10) exposes the sensitive unit 2 to a sample gas in a predetermined measurement period.

The temperature control element 3 heats and/or cools the sensitive unit 2.

The temperature controller 51 controls the temperature of the sensitive unit 2 by controlling the temperature control element 3. The temperature controller 51 controls the temperature control element 3 to cause the temperature of the sensitive unit 2 exposed to the sample gas to vary in a temperature variation pattern including at least one temperature rising period and at least one temperature falling period. The temperature rising period is a period in which the temperature of the sensitive unit 2 rises. The temperature falling period is a period in which the temperature of the sensitive unit 2 falls.

The determiner 55 determines an air quality condition of the sample gas. The determiner 55 determines the air quality condition of the sample gas based on a variation pattern in the electrical characteristic value with the temperature of the sensitive unit 2 exposed to the sample gas caused to vary in the temperature variation pattern.

As used herein, the electrical characteristic value of the sensitive unit 2 may be, for example, an electrical resistance or a current value or voltage value corresponding to the electrical resistance. Also, as used herein, to determine the air quality condition of a sample gas may refer to either determining whether molecules to detect are present in the sample gas (in other words, determining whether molecules to detect are included in the sample gas at a concentration greater than a predetermined concentration) or determining the type of the molecules to detect which are present in the sample gas. Furthermore, the molecules to detect do not have to be a single type of molecules. If there are multiple types of molecules to detect, then "to determine the air quality condition" may refer to detecting the presence or absence of each of the multiple types of molecules and determining the concentration thereof, for example. Still alternatively, to determine the air quality condition may also refer to determining the odor quality (such as a pleasant odor or an unpleasant odor) of the sample gas.

In the air quality determination system 1 according to this embodiment, the temperature controller 51 controls the temperature control element 3 to cause the temperature of the sensitive unit 2 exposed to the sample gas to vary in a temperature variation pattern including a temperature rising period and a temperature falling period. The determiner 55 determines the air quality condition of the sample gas based on a variation pattern in the electrical characteristic value with the temperature of the sensitive unit 2 exposed to the sample gas caused to vary in the temperature variation pattern including the temperature rising period and the temperature falling period. In this embodiment, when the electrical characteristic value of the sensitive unit 2 changes in response to a molecule to which the sensitive unit 2 has sensitivity, the variation pattern of the electrical characteristic value in the temperature rising period and the temperature falling period changes from a variation pattern in a state where there are no molecules to which the sensitive unit 2 has sensitivity. This enables the determiner 55 to determine the air quality condition of the sample gas based on a variation in the variation pattern of the electrical characteristic value in the temperature rising period and the temperature falling period. Consequently, this enables reducing the chances of determining the air quality condition erroneously due to variation components caused by the temperature, thereby reducing the chances of causing a decline in the accuracy of the air quality condition determined.

(2) Details (2.1) Configuration

As shown in FIG. 1, the air quality determination system 1 according to this embodiment includes the sensitive unit 2, the temperature control element 3, and the determination module 5. The determination module 5 includes the temperature controller 51 and a processor 50 including the determiner 55. In addition, the air quality determination system 1 further includes a temperature sensor 4 and the sensor housing chamber 10. The determination module 5 further includes a storage device 52 and a display device 57.

The sensitive unit 2, the temperature control element 3, and the temperature sensor 4 are housed in a housing space 11 inside the sensor housing chamber 10. The sensor housing chamber 10 has an inlet port 12 for introducing the air into the housing space 11 therethrough and an outlet port 13 for exhausting the air out of the housing space 11. The sample gas is introduced through the inlet port 12 into the housing space 11 and exhausted to the external environment through the outlet port 13. In this embodiment, an exposure unit for exposing the sensitive unit 2 to the sample gas in a predetermined measurement period is implemented as the sensor housing chamber 10 having the housing space 11. The sensitive unit 2 housed in the housing space 11 is exposed to the sample gas by introducing the sample gas into the housing space 11 of the sensor housing chamber 10 that serves as the exposure unit in a predetermined measurement period. That is to say, the air quality determination system 1 includes the housing space 11 as the exposure unit for exposing the sensitive unit 2 to the sample gas in the predetermined measurement period. Optionally, the air quality determination system 1 may include, for example, a blower for supplying the sample gas into the housing space 11.

Inside the housing space 11, an electrothermal element 31 having a plate shape is disposed as the temperature control element 3 and the sensitive unit 2 is disposed on the electrothermal element 31. In addition, inside the housing space 11, a temperature sensor 4 such as a thermistor is disposed in the vicinity of the sensitive unit 2. The temperature sensor 4 is a sensor for detecting the temperature of the sensitive unit 2. In this embodiment, the temperature sensor 4 detects the temperature of the sensitive unit 2 indirectly by detecting the temperature in the environment surrounding the sensitive unit 2 (i.e., the temperature of the housing space).

The electrical characteristic value of the sensitive unit 2 changes in reaction to one or more types of molecules to which the sensitive unit 2 has sensitivity. In this embodiment, the sensitive unit 2 includes a plurality of sensitive elements Ax (where x is a natural number) having mutually different sensitivities. In this embodiment, the sensitive unit 2 includes sixteen sensitive elements Ax, which will be hereinafter sometimes referred to as sensitive elements A1-A16 (refer to FIG. 2). The sixteen sensitive elements A1-A16 are arranged in four rows and four columns on a board 20 having a flat plate shape.

Figure 2:
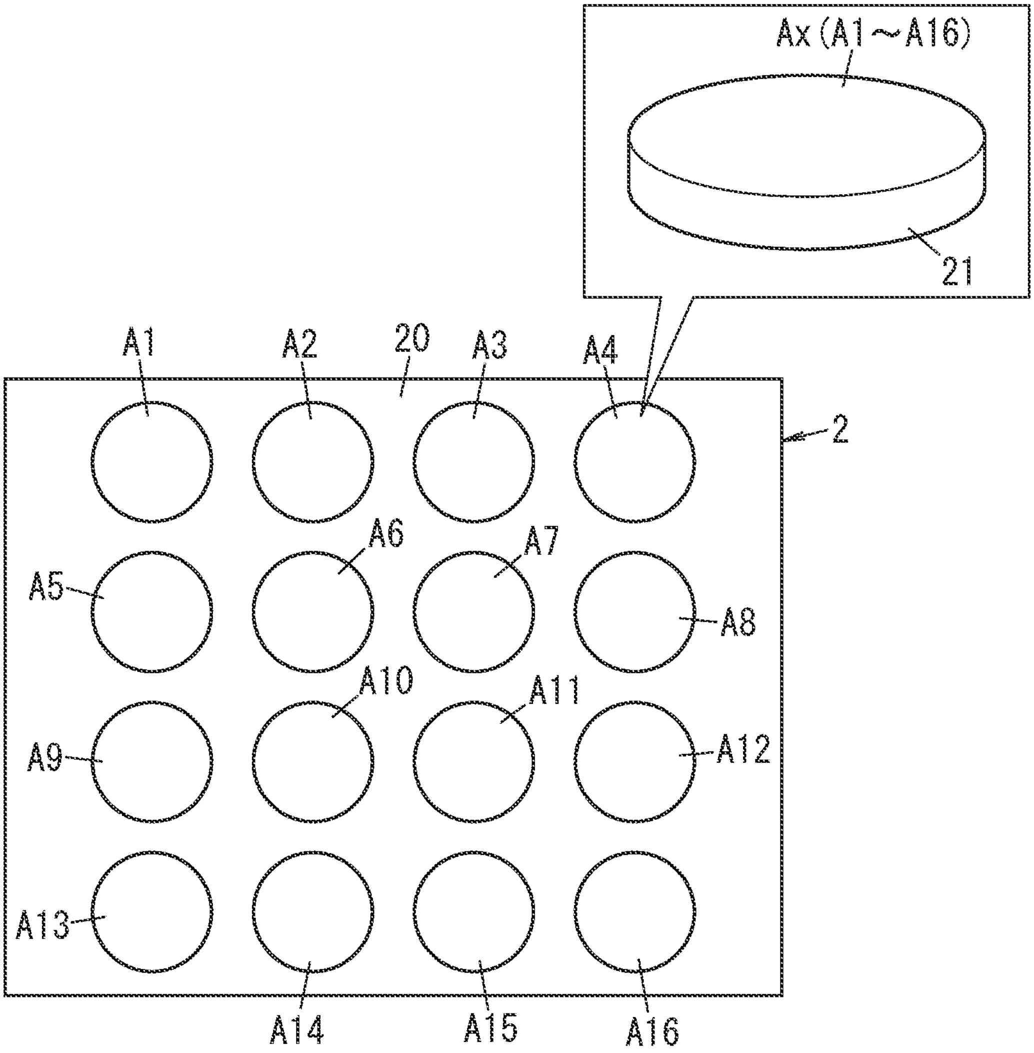
FIG. 2 schematically illustrates a sensitive unit included in the air quality determination system.

In this case, each of the sensitive elements Ax includes: an organic composition 21 formed out of an organic material into a disk shape; and conductive particles 22 dispersed in the organic composition 21 and is formed in a film shape as shown in FIGS. 2 and 3. When the sensitive element Ax is exposed to a sample gas including molecules to detect, the organic composition 21 absorbs the molecules to detect and expands. In FIG. 3, the portion on the left-hand side illustrates a state of the sensitive element Ax that has not absorbed the molecules M1 to detect yet and the portion on the right-hand side illustrates a state of the sensitive element Ax that has absorbed the molecules M1 to detect. When the sensitive element Ax absorbs the molecules M1 to detect, the organic composition 21 expands. Thus, after the sensitive element Ax has absorbed the molecules M1 to detect, the interval between the conductive particles 22 widens, and electrical resistance of the sensitive element Ax increases, compared to the interval and the electrical resistance before the sensitive element Ax absorbs the molecules M1 to detect. In this embodiment, the molecules to detect are odor molecules such as benzaldehyde, nonanal, and pyrrole. That is to say, the sensitive element Ax includes an organic composition 21 having sensitivity to odor molecules. When the sensitive unit 2 is exposed to a sample gas including the odor molecules, the organic composition 21 adsorbs the odor molecules and expands, thus causing an increase in the electrical resistance of the organic composition 21.

Note that the sensitive element Ax has temperature dependence that causes an electrical characteristic value (electrical resistance) thereof to vary according to the temperature. In this case, there are two types of sensitive elements Ax, namely, a sensitive element Ax, of which the electrical resistance increases as the temperature rises and which has a positive resistance coefficient (hereinafter referred to as a "positive characteristic sensitive element") and a sensitive element Ax, of which the electrical resistance decreases as the temperature rises and which has a negative resistance coefficient (hereinafter referred to as a "negative characteristic sensitive element").

Figure 4:
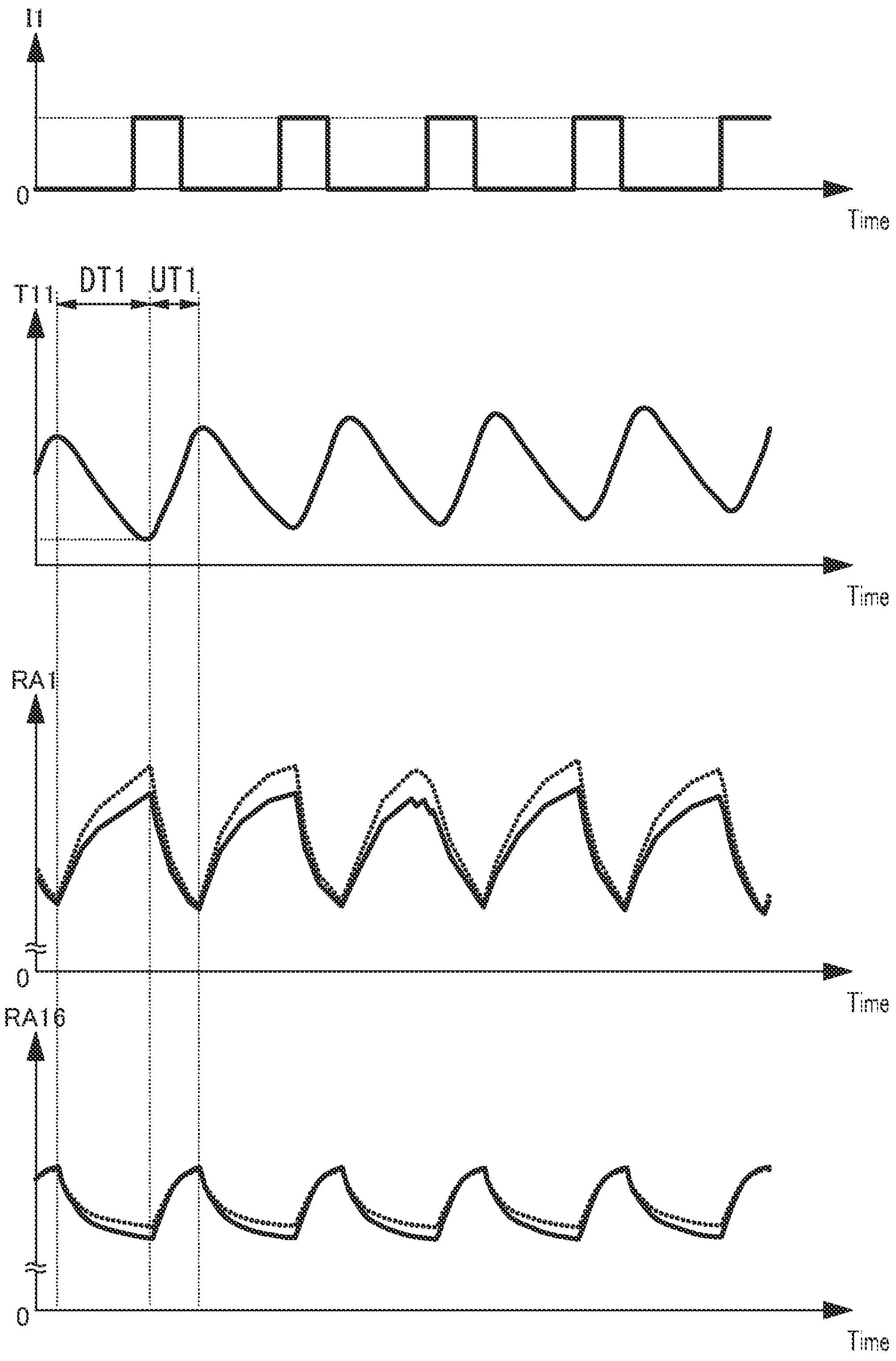
FIG. 4 is a waveform chart showing a current flowing through a temperature control element included in the air quality determination system, the temperature of a housing space, the output of a negative characteristic sensitive element, and the output of a positive characteristic sensitive element.

In this embodiment, the sensitive unit 2 includes negative characteristic sensitive elements having a negative resistance coefficient in a temperature range equal to or higher than −20° C. and equal to or lower than 50° C. The sensitive elements A1-A11 correspond to negative characteristic sensitive elements. The sensitive unit 2 also includes positive characteristic sensitive elements having a positive resistance coefficient in a temperature range equal to or higher than −20° C. and equal to or lower than 50° C. The sensitive elements A12-A16 correspond to positive characteristic sensitive elements. The temperature controller 51 controls the temperature of the sensitive unit 2 by causing pulses of a current Il to flow through the electrothermal element 31 as shown in FIG. 4. Causing such pulses of a current Il to flow through the electrothermal element 31 allows the temperature of the sensitive unit 2 to be controlled in a temperature variation pattern in which a temperature rising period UT1 in which the temperature of the sensitive unit 2 rises and a temperature falling period DT1 in which the temperature of the sensitive unit 2 falls alternate with each other repeatedly. In this case, as the temperature of the sensitive unit 2 varies, the temperature T11 in the housing space 11 also varies in a temperature variation pattern in which a temperature rising period UT1 in which the temperature rises and a temperature falling period DT1 in which the temperature falls alternate with each other repeatedly. Note that the temperature rising period UT1 needs to be long enough to desorb the odor molecules and may be a few ten seconds, for example, but may be changed as appropriate. The temperature falling period DT1 needs to be long enough to stabilize the variation in the electrical characteristic value due to adsorption of the odor molecules and may be a few ten seconds, for example, but may be changed as appropriate.

The sensitive element A1 is a negative characteristic sensitive element, of which the resistance value decreases as the temperature rises. Thus, if the temperature of the sensitive element A1 is caused to vary in the temperature variation pattern, then the resistance value RA1 of the sensitive element A1 varies in a pattern in which the resistance value RA1 decreases as the temperature rises in the temperature rising period UT1 and increases as the temperature falls in the temperature falling period DT1. In this case, if the sensitive element A1 is exposed to a sample gas including the odor molecules, the resistance value RA1 decreases due to desorption of the odor molecules in the temperature rising period UT1 and increases due to absorption of the odor molecules in the temperature falling period DT1. Consequently, the resistance value RA1 of the sensitive element A1 varies in a variation pattern in which variation components corresponding to the quantity of the odor molecules adsorbed into the sensitive element A1 are superposed on the variation components caused by the temperature variation. In FIG. 4, the resistance value RA1 in a situation where the sensitive element A1 is exposed to a standard gas (such as nitrogen gas) including no odor molecules is indicated by the solid curve and the resistance value RA1 in a situation where the sensitive element A1 is exposed to a sample gas including odor molecules is indicated by the dotted curve.

The sensitive element A16 is a positive characteristic sensitive element, of which the resistance value increases as the temperature rises. Thus, if the temperature of the sensitive element A16 is caused to vary in the temperature variation pattern, then the resistance value RA16 of the sensitive element A16 varies in a pattern in which the resistance value RA16 increases as the temperature rises in the temperature rising period UT1 and decreases as the temperature falls in the temperature falling period DT1. In this case, if the sensitive element A16 is exposed to a sample gas including the odor molecules, the resistance value RA16 decreases due to desorption of the odor molecules in the temperature rising period UT1 and increases due to absorption of the odor molecules in the temperature falling period DT1. Consequently, the resistance value RA16 of the sensitive element A16 varies in a variation pattern in which variation components corresponding to the quantity of the odor molecules adsorbed into the sensitive element A16 are superposed on the variation components (that cause an increase in the temperature rising period UT1 and a decrease in the temperature falling period DT1) caused by the temperature variation. In FIG. 4, the resistance value RA1 in a situation where the sensitive element A16 is exposed to a standard gas (such as nitrogen gas) is indicated by the solid curve and the resistance value RA16 in a situation where the sensitive element A16 is exposed to a sample gas including odor molecules is indicated by the dotted curve.

In this embodiment, the temperature control element 3 is an electrothermal element 31 for heating the sensitive unit 2 and the temperature controller 51 changes the temperature of the sensitive unit 2 from a first temperature that is the ambient temperature to a second temperature higher than the ambient temperature, or vice versa, by controlling the temperature control element 3. Note that the second temperature is set at a temperature higher by, for example, about 7° C. to about 35° C. than the first temperature. The difference between the first temperature and the second temperature is preferably wide enough to cause the odor molecules to be adsorbed or desorbed and preferably narrow enough to minimize the variation in the resistance value due to the temperature variation. In this example, the difference between the first temperature and the second temperature needs to at least equal to or greater than 7° C. and at most equal to or less than 35° C. Also, the difference between the first temperature and the second temperature is preferably equal to or greater than 20° C. and equal to or less than 35° C. and more preferably equal to or greater than 20° C. and equal to or less than 25° C.

For example, if the first temperature is 25° C., then the temperature controller 51 controls the temperature of the sensitive unit 2 between 25° C. as the first temperature and 50° C. as a second temperature. On the other hand, if the first temperature is 0° C., then the temperature controller 51 controls the temperature of the sensitive unit 2 between 0° C. as the first temperature and 25° C. as a second temperature. Furthermore, if the first temperature is −20° C., then the temperature controller 51 controls the temperature of the sensitive unit 2 between −20° C. as the first temperature and 5° C. as a second temperature. Note that the temperature controller 51 does not have to change the temperature of the sensitive unit 2 in such a temperature variation pattern. Rather, the temperature controller 51 may change the temperature of the sensitive unit 2 in such a temperature variation pattern that causes the variation pattern of the output of the sensitive unit 2 to change significantly according to the air quality condition of the sample gas.

The following Table 1 shows the respective compositions of the sixteen sensitive elements A1-A16. In Table 1, the percentage of the side chain shown in the "side chain feature" column indicates the proportion to the entire side chain:

TABLE 1

| Sensitive element | Main chain | Side chain feature |
|---|---|---|
| A1 | Siloxane | Methyl |
| A2 | Siloxane | Methyl, 10% phenyl |
| A3 | Siloxane | Methyl, cyano propyl (≤20%) |
| A4 | Siloxane | Methyl, 20% phenyl |
| A5 | Siloxane | Methyl, 35% phenyl |
| A6 | Siloxane | Methyl, 50% phenyl |
| A7 | Siloxane | Methyl, 7% phenyl, 7% cyano propyl |
| A8 | Siloxane | Methyl, 65% phenyl |
| A9 | Siloxane | Methyl, 75% phenyl |
| A10 | Siloxane | Methyl, 50% fluoropropyl |
| A11 | Siloxane | Methyl, 25% cyano propyl, 25% phenyl |
| A12 | Siloxane | Methoxy polyethylene glycol propyl, phenyl |
| A13 | PEG modified with terephthalic acid | Nitro |
| A14 | Siloxane | 90% cyano propyl, 10% phenyl |
| A15 | Siloxane | Cyano propyl |
| A16 | Siloxane | Dicyano allyl |

The organic composition 21 included in the sensitive elements A1-A11 as negative characteristic sensitive elements includes siloxane on a main chain thereof and a methyl group on a side chain thereof. The organic composition 21 included in the sensitive elements A1-A11 has a structure in which the structure expressed by the following chemical formula 1 and the structure expressed by the following chemical formula 2 are coupled to each other so that Si and O are arranged alternately. In the following chemical formulae 1 and 2, any of the plurality of R1 includes a methyl group.

(1)

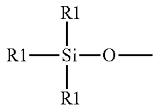

(2)

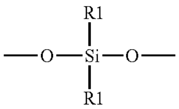

The positive characteristic sensitive element includes at least one of the first to fourth sensitive elements.

The sensitive element A12 as the first sensitive element includes an organic composition 21 having siloxane on a main chain thereof and having no methyl group on a side chain thereof but having a polyethylene glycol group on the side chain thereof (specifically, having a methoxy polyethylene glycol propyl group and a phenyl group on a side chain thereof). Note that the sensitive element A12 has the structure expressed by the following chemical formula 3, where m may be, for example, equal to or greater than 2 and equal to or less than 1000 and n may be, for example, equal to or greater than 2 and equal to or less than 1000:

(3)

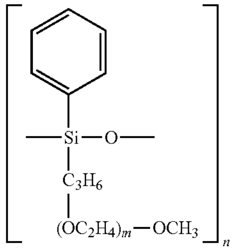

The sensitive element A13 as the second sensitive element includes an organic composition 21 having polyethylene glycol (PEG) modified with terephthalic acid on a main chain thereof and having no methyl group on a side chain thereof but having a nitro group on the side chain thereof. Note that the sensitive element A13 has the structure expressed by the following chemical formula 4, where m may be, for example, equal to or greater than 2 and equal to or less than 1000 and n may be, for example, equal to or greater than 2 and equal to or less than 1000:

(4)

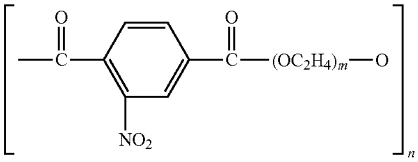

The sensitive elements A14, A15 as the third sensitive elements each include an organic composition 21 having siloxane on a main chain thereof and having no methyl group on a side chain thereof but having a cyano propyl group on the side chain thereof. The sensitive element A14 has the structure expressed by the following chemical formula 5. The organic composition 21 of the sensitive element A14 has, on a side chain thereof, 90% cyano propyl group and 10% phenyl group. The sensitive element A15 has the structure expressed by the following chemical formula 6. The organic composition 21 of the sensitive element A15 has, on a side chain thereof, 100% cyano propyl group.

(5)

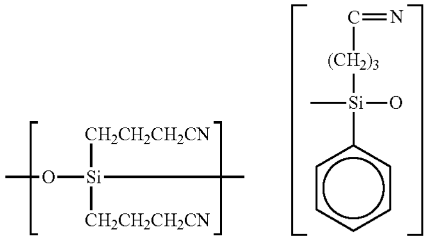

(6)

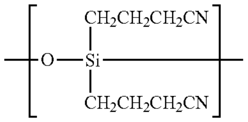

The sensitive element A16 as the fourth sensitive element includes an organic composition 21 having siloxane on a main chain thereof and having no methyl group on a side chain thereof but having a cyano allyl group on the side chain thereof (specifically, a dicyano allyl group). The sensitive element A16 has the structure expressed by the following chemical formula 7.

(7)

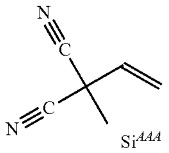

Figure 5:
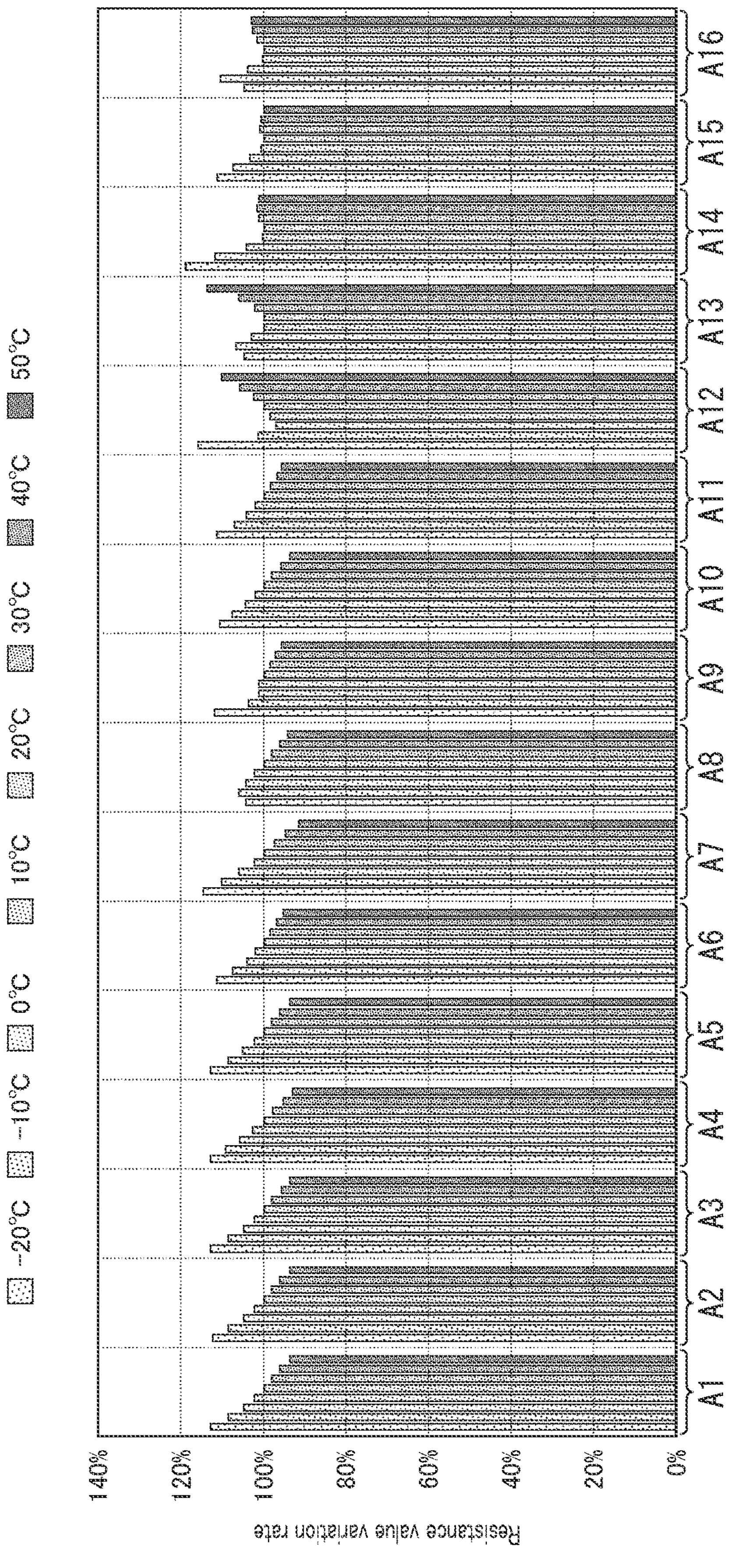
FIG. 5 is a graph showing results of measurement of resistance values that varied according to the temperature with respect to sixteen sensitive elements included in the air quality determination system.

FIG. 5 shows exemplary results of respective resistance values of the sixteen sensitive elements A1-A16 which were measured with the sensitive elements A1-A16 exposed to a standard gas (such as nitrogen gas). In FIG. 5, with the resistance value at 20° C. used as a reference value, the resistance values at temperatures of −20° C., −10° C., 0° C., 10° C., 30° C., 40° C., and 50° C. are indicated as percentages with respect to each of the sensitive elements A1-A16. These results of measurement reveal that each of the sensitive elements A14-A16 caused little variation in resistance value according to the temperature within a temperature range from 20° C. to 50° C. Thus, causing the temperature of the sensitive elements A14-A16 to vary within the temperature range equal to or higher than 20° C. and equal to or lower than 50° C. enables determining the air quality condition accurately based on the variation pattern in the resistance values of the sensitive elements A14-A16.

In this embodiment, the sensitive unit 2 includes the first to fourth sensitive elements A12-A16 as positive characteristic sensitive elements. However, the sensitive unit 2 does not have to include all of the first to fourth sensitive elements A12-A16 but may include one or more of the first to fourth sensitive elements A12-A16.

The temperature controller 51 controls the temperature of the sensitive unit 2 by controlling, in response to a control signal supplied from the processor 50, the temperature control element 3 as an electrothermal element 31 such as a heater. The temperature controller 51 acquires, based on a result of detection by the temperature sensor 4 before heating is started by the temperature control element 3, an environmental temperature and uses the environmental temperature thus acquired as a first temperature. In addition, the temperature controller 51 also uses a temperature higher than the first temperature by a predetermined temperature (e.g., 25° C.) as a second temperature. Then, the temperature controller 51 controls, based on the result of detection by the temperature sensor 4, the temperature control element 3 such that the temperature of the sensitive unit 2 exposed to the sample gas varies in a temperature variation pattern including at least one temperature rising period UT1 in which the temperature rises to the second temperature and at least one temperature falling period DT1 in which the temperature falls to the first temperature. In this embodiment, the temperature controller 51 repeatedly raises and lowers the temperature of the sensitive unit 2 by repeating the temperature variation pattern, including one temperature rising period UT1 and one temperature falling period DT1, in response to a control signal supplied from the processor 50. In this case, in a situation where the sensitive unit 2 is exposed to a sample gas including molecules M1 to which the sensitive unit 2 has sensitivity, as the temperature of the sensitive unit 2 rises in the temperature rising period UT1, the molecules M1 absorbed into the organic composition 21 desorb, thus causing a decrease in electrical resistance as an electrical characteristic value of the sensitive unit 2. Thereafter, as the temperature of the organic composition 21 falls in the temperature falling period DT1, the organic composition 21 adsorbs the molecules M1, thus causing an increase in resistance value as an electrical characteristic value of the sensitive unit 2.

The storage device 52 includes one or more storage devices. Examples of the storage device include a RAM, a ROM, and an EEPROM. The storage device 52 stores, for example, a learned model MD1 for use to determine the air quality condition of the sample gas. The learned model MD1 is generated by learning the relationship between the variation pattern of the output of the sensitive unit 2 and the air quality condition of the sample gas, using, as learning data, the variation pattern of the output of the sensitive unit 2 when a first condition and a second condition are changed. The first condition is a condition about a gas to which the sensitive unit 2 is exposed. The second condition is a condition about the temperature variation pattern in which the temperature of the sensitive unit 2 is raised and lowered. The learned model MD1 may be generated by the air quality determination system 1. Alternatively, the learned model MD1 may also be generated by a learning system other than the air quality determination system 1.

The display device 57 may include, for example, a display device such as a liquid crystal display. The display device 57 displays the decision provided by the processor 50. For example, the display device 57 indicates whether there are any odor molecules in the sample gas and also indicates, if there are any odor molecules, the quantity and quality of the odor molecules.

The processor 50 is a control circuit for controlling the operation of the air quality determination system 1. The processor 50 may be implemented as a computer system including one or more processors (microprocessors) and one or more memories. That is to say, the functions of the processor 50 are performed by making the one or more processors execute one or more programs (applications) stored in the one or more memories. In this embodiment, the program is stored in advance in the memory of the processor 50 or the storage device 52. Alternatively, the program may also be downloaded via a telecommunications line such as the Internet or distributed after having been stored in a non-transitory storage medium such as a memory card.

As shown in FIG. 1, the processor 50 includes an acquirer 53, a learner 54, a determiner 55, and an outputter 56. In FIG. 1, none of the acquirer 53, learner 54, determiner 55, and outputter 56 has a substantive configuration but each of these units 53-56 just represents a function performed by the processor 50.

The acquirer 53 acquires, while the temperature controller 51 is supplying pulses of a current to the temperature control element 3, data about the temperature variation pattern of the sensitive unit 2 detected by the temperature sensor 4 and pulse outputs PL1-PL16 (refer to FIG. 6) of the sensitive elements A1-A16 for one cycle including one temperature rising period UT1 and one temperature falling period DT1. Note that a constant DC voltage is applied to each of the sensitive elements A1-A16 and the acquirer 53 acquires the variation in the electrical resistance of each of the sensitive elements A1-A16 as a variation in a current flowing through the sensitive element A1-A16. Thus, the pulse outputs PL1-PL16 become current signals, of which the magnitudes vary according to the electrical resistances of the sensitive elements A1-A16, respectively.

Figure 6:
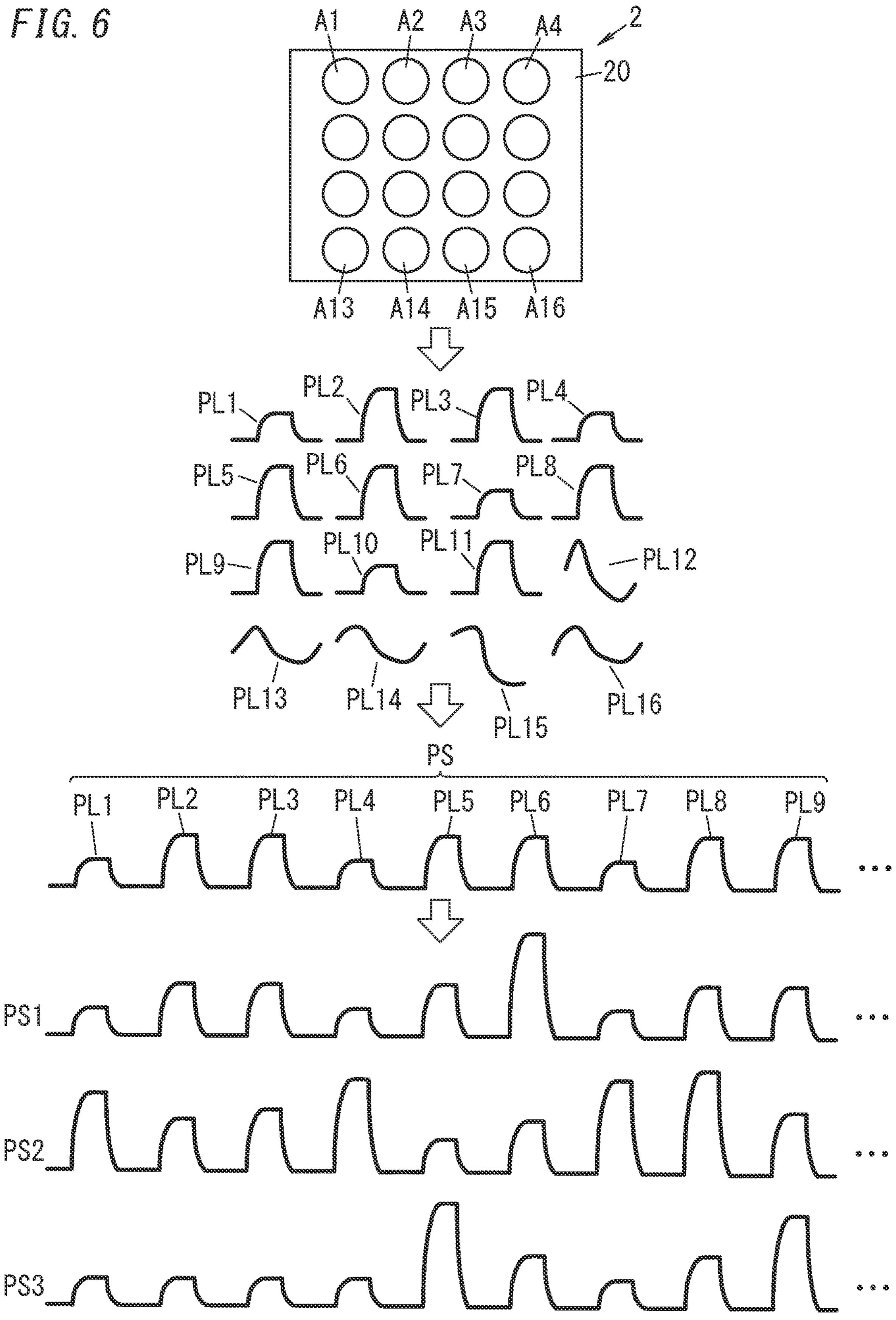
FIG. 6 illustrates a process in which a plurality of sensitive elements included in the air quality determination system provides output data.

When acquiring the data about the temperature variation pattern of the sensitive unit 2 and pulse outputs PL1-PL16 of the sensitive elements A1-A16 for one cycle, the acquirer 53 acquires, as the output data PS (i.e., a variation pattern of the electrical characteristic value) of the sensitive unit 2, a pulse train in which the pulse outputs PL1-PL16 are connected to each other in a predetermined order. The output data PS1-PS3 shown in FIG. 6 is an example of the output data PS in a state where the sensitive unit 2 is exposed to three types of sample gases having mutually different compositions. The sixteen sensitive elements A1-A16 exhibit mutually different sensitivities to the molecules to detect. Thus, the output data PS1-PS3 are pulse trains having mutually different variation patterns of the electrical characteristic value.

Figure 7:
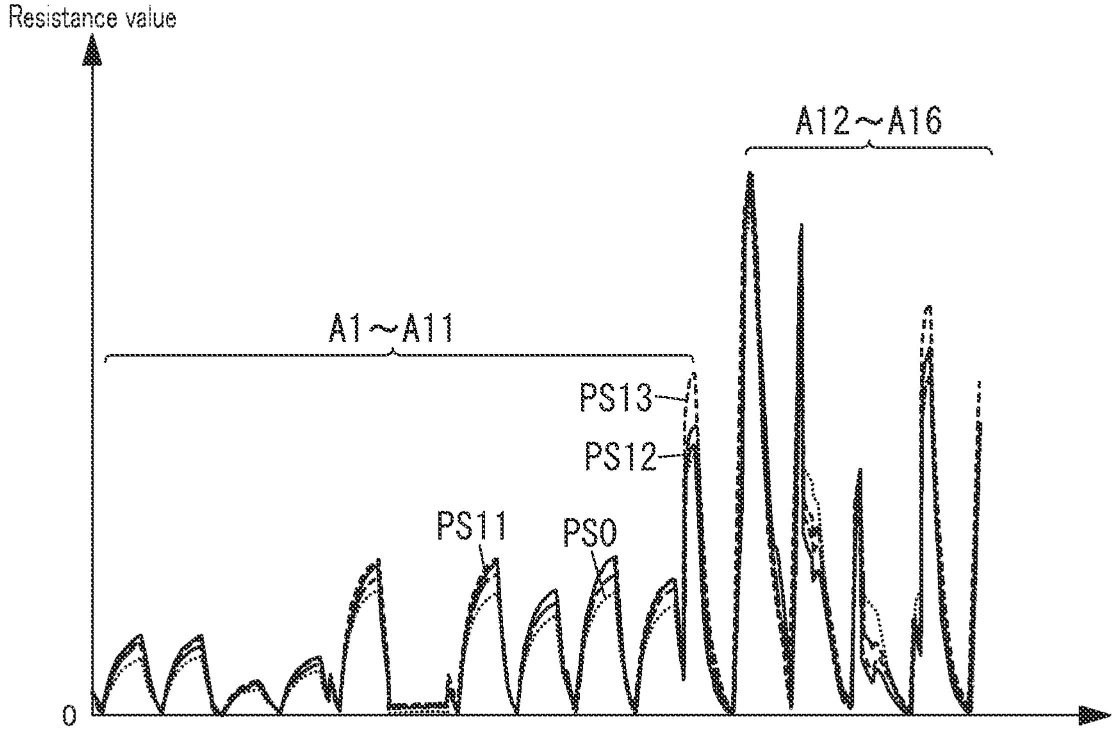
FIG. 7 shows how the output data of the sensitive unit of the air quality determination system changed when the temperature of the sensitive unit was caused to vary within a temperature range from 25° C. to 50° C.
Figure 8:
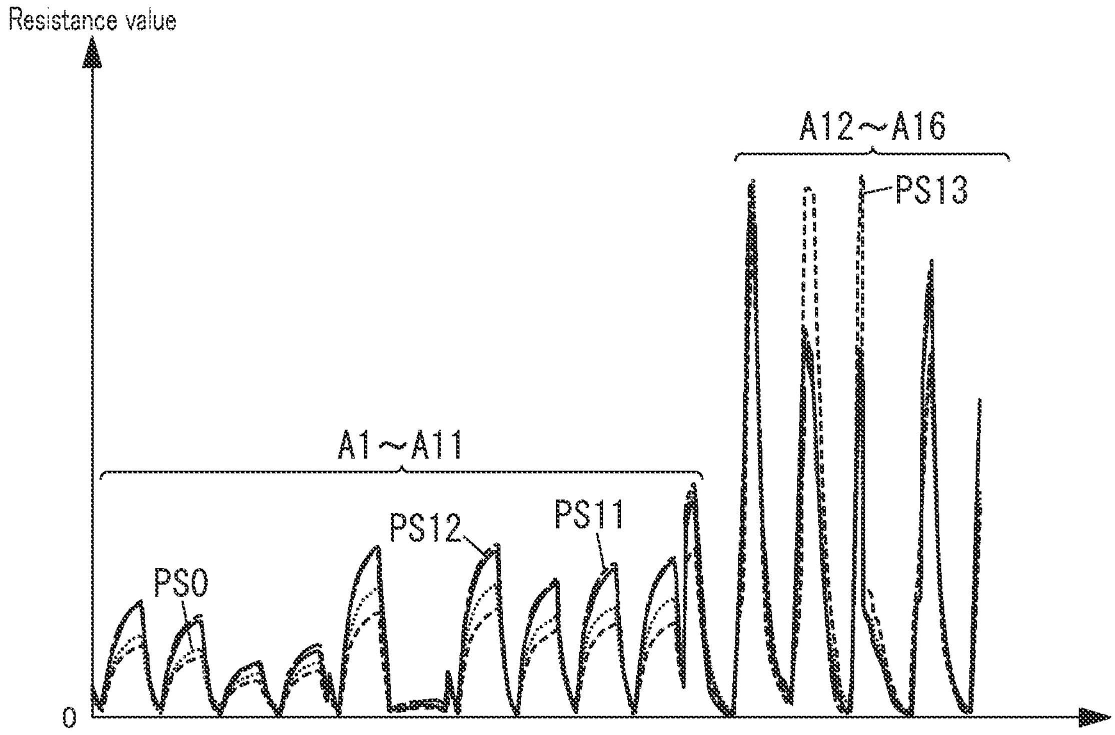
FIG. 8 shows how the output data of the sensitive unit of the air quality determination system changed when the temperature of the sensitive unit was caused to vary within a temperature range from 0° C. to 250° C.
Figure 9:
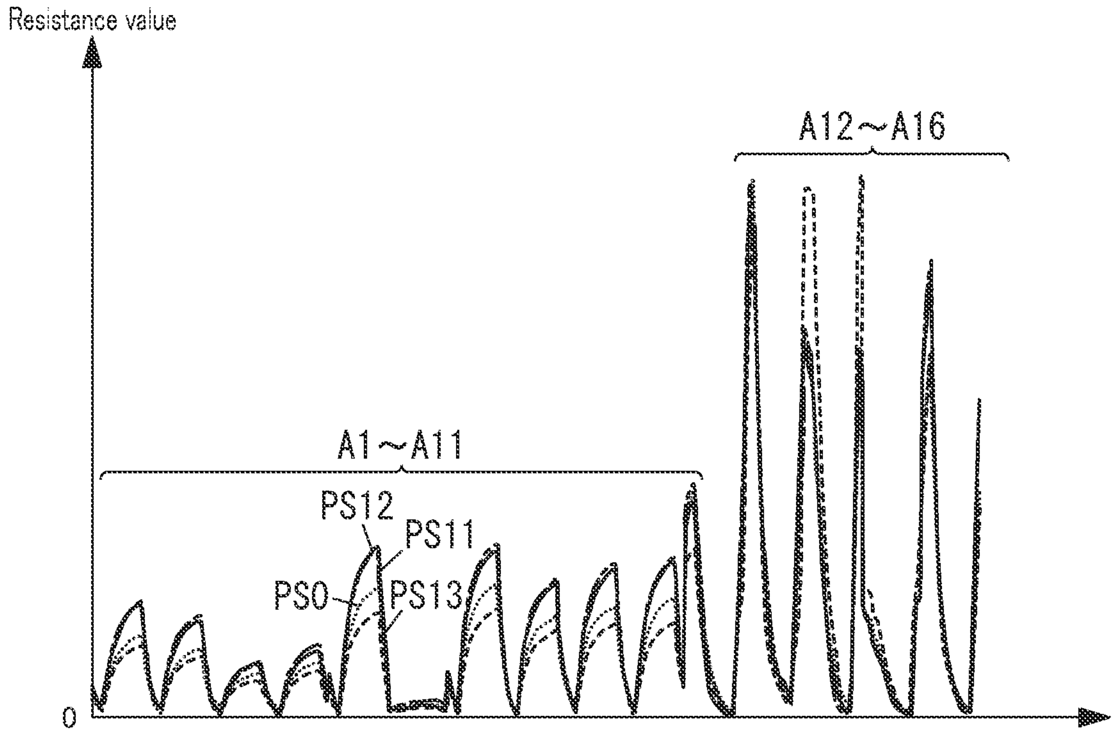
FIG. 9 shows how the output data of the sensitive unit of the air quality determination system changed when the temperature of the sensitive unit was caused to vary within a temperature range from −20° C. to 5° C.

FIGS. 7-9 show exemplary output data of the sensitive unit 2 to be obtained in a state where the sensitive unit 2 is exposed to three types of sample gases including three types of odor molecules and a standard gas. PS0 denotes the standard output data of the sensitive unit 2 exposed to the standard gas. PS 11 denotes output data obtained in a state where the sensitive unit 2 is exposed to a sample gas including 2 ppm of benzaldehyde. PS 12 denotes output data obtained in a state where the sensitive unit 2 is exposed to a sample gas including 2 ppm of nonanal. PS13 denotes output data obtained in a state where the sensitive unit 2 is exposed to a sample gas including 2 ppm of pyrrole. Specifically, FIG. 7 shows the output data collected when the temperature of the sensitive unit 2 was caused to vary within a temperature range equal to or higher than 20° C. and equal to or lower than 50° C. FIG. 8 shows the output data collected when the temperature of the sensitive unit 2 was caused to vary within a temperature range equal to or higher than 0° C. and equal to or lower than 25° C. FIG. 9 shows the output data collected when the temperature of the sensitive unit 2 was caused to vary within a temperature range equal to or higher than −20° C. and equal to or lower than 5° C.

As can be seen from FIG. 7, if the temperature of the sensitive unit 2 is caused to vary within a temperature range equal to or higher than 20° C. and equal to or lower than 50° C., the difference between the output data collected when the sensitive unit 2 is exposed to the standard gas and the output data collected when the sensitive unit 2 is exposed to a sample gas including the odor molecules becomes more significant in the positive characteristic sensitive elements (namely, the sensitive elements A12-A16) than in the negative characteristic sensitive elements (namely, the sensitive elements A1-A11). Thus, if the temperature of the sensitive unit 2 is caused to vary within a temperature range equal to or higher than 20° C. and equal to or lower than 50° C., then the air quality condition of the sample gas may be determined more easily based on the output data collected from the positive characteristic sensitive elements (namely, the sensitive elements A12-A16). That is to say, the temperature controller 51 preferably changes the temperature of the positive characteristic sensitive elements in a temperature variation pattern including a temperature rising period UT1 in which the temperature of the positive characteristic sensitive elements is raised within the temperature range equal to or higher than 20° C. and equal to or lower than 50° C. and a temperature falling period DT1 in which the temperature of positive characteristic sensitive elements is lowered within the temperature range.

As can be seen from FIGS. 8 and 9, if the temperature of the sensitive unit 2 is caused to vary within a temperature range equal to or higher than −20° C. and equal to or lower than 20° C., the difference between the output data collected when the sensitive unit 2 is exposed to the standard gas and the output data collected when the sensitive unit 2 is exposed to a sample gas including the odor molecules becomes more significant in the negative characteristic sensitive elements (namely, the sensitive elements A1-A11) than in the positive characteristic sensitive elements (namely, the sensitive elements A12-A16). Thus, if the temperature of the sensitive unit 2 is caused to vary within a temperature range equal to or higher than −20° C. and equal to or lower than then the air quality condition of the sample gas may be determined more easily based on the output data collected from the negative characteristic sensitive elements (namely, the sensitive elements A1-A11). That is to say, the temperature controller 51 preferably changes the temperature of the negative characteristic sensitive elements in a temperature variation pattern including a temperature rising period UT1 in which the temperature of the negative characteristic sensitive elements is raised within a temperature range equal to or higher than −20° C. and equal to or lower than 20° C. and a temperature falling period DT1 in which the temperature of negative characteristic sensitive elements is lowered within the temperature range equal to or higher than −20° C. and equal to or lower than 20° C.

As can be seen from the foregoing description, the sensitive unit 2 according to this embodiment includes the sensitive elements A1-A11, of which the resistance value varies significantly due to the adsorption or desorption of odor molecules within the temperature range equal to or higher than −20° C. and equal to or lower than 20° C. and the sensitive elements A12-A16, of which the resistance value varies significantly due to the adsorption or desorption of odor molecules within the temperature range equal to or higher than 20° C. and equal to or lower than Thus, if the temperature of the sensitive unit 2 is changed, the resistance value varies significantly due to the adsorption or desorption of the odor molecules within the temperature variation range of the sensitive unit 2. That is to say, this enables determining the air quality condition of the sample gas based on the pulse outputs of the sensitive elements having high sensitivity to the odor molecules. Consequently, the air quality determination system 1 may determine the air quality condition of the sample gas accurately.

The learner 54 generates a learned model MD1. That is to say, the learner 54 is in charge of the learning phase. In the learner 54, data about the temperature variation patterns acquired by the acquirer 53 and the output data PS of the sensitive elements A1-A16 are accumulated as learning data for use to generate the learned model MD1. The learner 54 generates the learned model MD1 based on the learning data thus collected. That is to say, the learner 54 uses the machine learning data acquired by the air quality determination system 1 to make an artificial intelligence program (algorithm) learn the relation between the variation patterns (output data PS) of the electrical characteristic values of the sensitive elements A1-A16 and the air quality condition of the sample gas. The artificial intelligence program is a machine learning model and may be, for example, a neural network as a type of a hierarchical model. The learner 54 makes the neural network make machine learning (such as deep learning) using the learning data, thereby generating the learned model MD1 and storing the learned model MD1 in the storage device 52. Optionally, the learner 54 may attempt to improve the performance of the learned model MD1 by making relearning using the learning data newly collected by the acquirer 53 after having generated the learned model MD1.

The determiner 55 is in charge of so-called "inference phase." The determiner 55 uses the learned model MD1 stored in the storage device 52 to determine, based on the output data PS acquired by the acquirer 53, the air quality condition of the sample gas. Specifically, the determiner 55 inputs, to the learned model generated by machine learning, the electrical characteristic values of the sensitive unit 2 in a state where the temperature controller 51 controls the temperature control element 3 such that the temperature of the sensitive unit 2 exposed to the sample gas changes in the temperature variation pattern, thereby determining the air quality condition of the sample gas. In this embodiment, the sensitive unit 2 includes the plurality of sensitive elements Ax (namely, the sensitive elements A1-A16). Thus, the determiner 55 determines the air quality condition of the sample gas based on the variation patterns of the electrical characteristic values of the plurality of sensitive elements Ax in a state where the temperatures of the plurality of sensitive elements Ax exposed to the sample gas are caused to vary in the temperature variation pattern. Furthermore, the determiner 55 inputs the measurement data of the temperature variation pattern detected by the temperature sensor 4 and then acquired by the acquirer 53 and the output data PS to the learned model MD1. The learned model MD1 makes inference based on the output data PS when the temperature of the sensitive unit 2 varies in the temperature variation pattern, thereby determining the air quality condition of the sample gas. As described above, in the temperature range equal to or higher than −20° C. and equal to or lower than the resistance values vary in reaction to the odor molecules more significantly in the negative characteristic sensitive elements than in the positive characteristic sensitive elements. Thus, the determiner 55 determines the air quality condition depending more heavily on the output data of the sensitive elements A1-A11. On the other hand, in the temperature range from 20° C. to 50° C., the resistance values vary in reaction to the odor molecules more significantly in the positive characteristic sensitive elements than in the negative characteristic sensitive elements. Thus, the determiner 55 determines the air quality condition depending more heavily on the output data of the sensitive elements A12-A16.

In this embodiment, the determiner 55 determines, as the air quality condition of the sample gas, whether the sample gas includes the odor molecules and also determines, if the answer is yes, whether the quantity of the odor molecules included in the sample gas is equal to or greater than a threshold value. Optionally, when deciding that the odor molecules be included in the sample gas, the determiner 55 may further determine the concentration of the odor molecules in the sample gas.

Note that the air quality determination system 1 does not have to include the learner 54. Alternatively, the determiner 55 may also perform the inference phase using a learned model MD1 generated by an external computer system.

The outputter 56 outputs the decision made by the determiner 55. Specifically, the outputter 56 outputs the decision made by the determiner 55 to the display device 57 to make the display device 57 display the decision made by the determiner 55. Note that the decision output by the outputter 56 does not have to be displayed on the display device 57. Alternatively, a decision about the presence or absence of the odor molecules may also be output as a sound using a buzzer or a loudspeaker.

Figure 19:
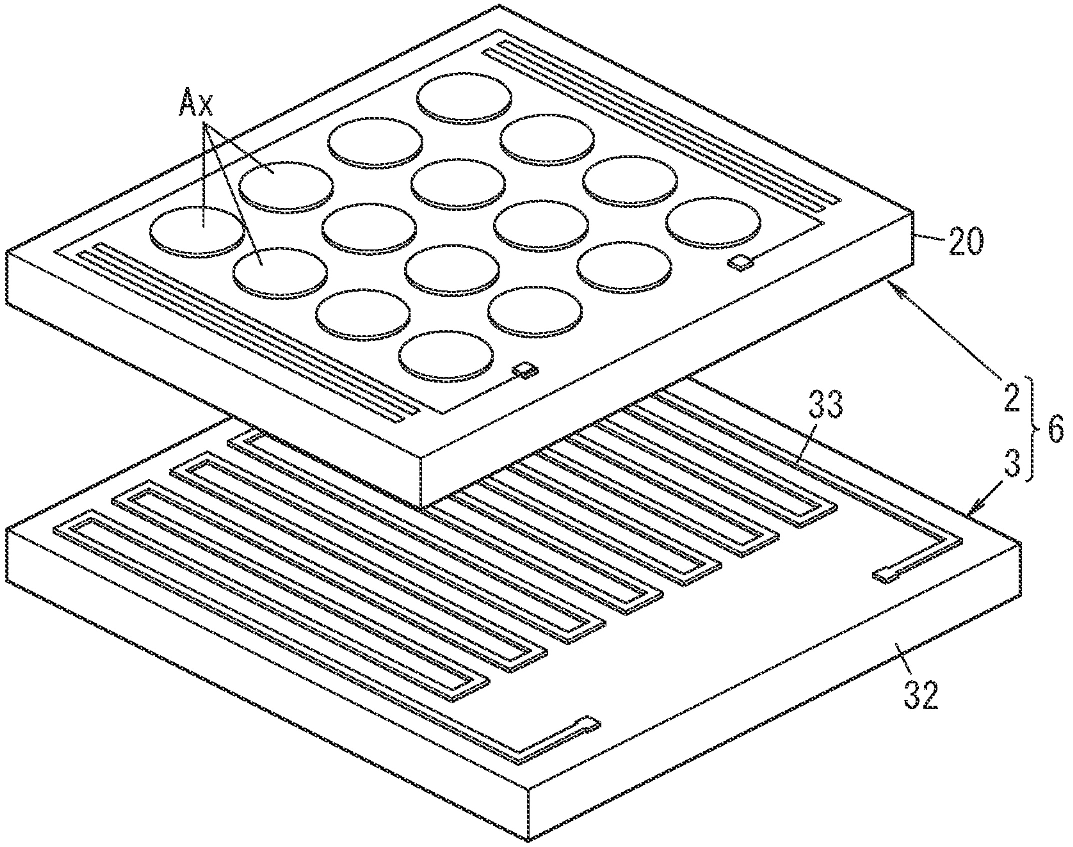
FIG. 19 is a schematic exploded perspective view of a sensor module included in an air quality determination system according to an exemplary embodiment.

In this embodiment, the sensitive unit 2 and the temperature control element 3 that are included in the air quality determination system 1 may be implemented as a single component (sensor module 6). FIG. 19 schematically illustrates the appearance of the sensor module 6. The sensor module 6 is formed as a single component by stacking the temperature control element 3, including a board 32 with a heater circuit 33 formed on a principal surface thereof, and the sensitive unit 2, including a board 20 with a plurality of sensitive elements Ax formed on a principal surface thereof, one on top of the other. In other words, the sensor module 6 includes the sensitive unit 2, of which the electrical characteristic value changes in reaction to one or more types of molecules, and the temperature control element 3 that heats and/or cools the sensitive unit 2. The temperature control element 3 generates heat by, for example, being energized by the determination module 5, thereby heating the sensitive unit 2. The temperature control element 3 causes the temperature of the sensitive unit 2 exposed to the sample gas in the predetermined measurement period to vary in a temperature variation pattern including at least one temperature rising period in which the temperature of the sensitive unit 2 rises and at least one temperature falling period in which the temperature of the sensitive unit 2 falls.

As can be seen, the sensor module 6 including the sensitive unit 2 and the temperature control element 3 is implemented as a multilayer stack formed by stacking the board 20 of the sensitive unit 2 and the board 30 of the temperature control element 3 one on top of the other. Thus, providing multiple types of sensor modules 6 for multiple different purposes allows the air quality determination system 1 to be used for a single or multiple purposes by disposing a single or multiple sensor modules 6 for any desired intended use in the housing space 11.

(2.2) Description of Operation

Figure 10:
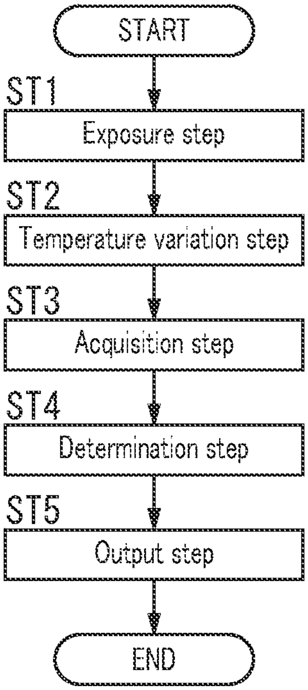
FIG. 10 is a flowchart showing a procedure of operation of the air quality determination system in an inference phase.

Next, it will be described with reference to the flowchart shown in FIG. 10 how the air quality determination system 1 according to this embodiment operates in the inference phase. Note that the flowchart of FIG. 10 shows only an exemplary air quality determination method according to this embodiment. Thus, the processing steps shown in FIG. 10 may be performed in a different order as appropriate, an additional processing step may be performed as appropriate, or at least one of the processing steps may be omitted as appropriate.

The user of the air quality determination system 1 may, for example, turn a power switch ON to activate the processor 50 and make the air quality determination system 1 start performing the operation of determining the air quality of a sample gas. The user of the air quality determination system 1 introduces the sample gas through the inlet port 12 into the housing space 11 and thereby exposes the sensitive unit 2 to the sample gas (in an exposure step ST1).

After the processor 50 has started performing the operation of determining the air quality, the processor 50 controls the temperature controller 51, thereby controlling the temperature of the sensitive unit 2 to cause the temperature of the sensitive unit 2 to vary in a temperature variation pattern in which the temperature rising period UT1 and the temperature falling period DT1 alternate with each other repeatedly (in a temperature variation step ST2).

At this point in time, the acquirer 53 acquires the variation pattern of the electrical characteristic value of the sensitive unit 2 in a state where the temperature of the sensitive unit 2 is varying in the temperature variation pattern described above (in an acquisition step ST3). Note that the acquirer 53 preferably acquires the variation pattern of the electrical characteristic value of the sensitive unit 2 at a timing when the sensitive unit 2 has gone through several temperature variation cycles, each including one temperature rising period UT1 and one temperature falling period DT1, since the temperature variation step ST2 started. This allows the acquirer 53 to acquire the variation pattern of the electrical characteristic value of the sensitive unit 2 in a state where the variation pattern of the electrical characteristic value of the sensitive unit 2 is stabilized.

Then, after the variation pattern of the electrical characteristic value has been acquired by the acquirer 53, the determiner 55 inputs, to the learned model MD1, data about the variation pattern of the electrical characteristic value that has been acquired by the acquirer 53 and data about the temperature variation pattern of the sensitive unit 2 that has been detected by the temperature sensor 4, thereby determining the air quality condition of the sample gas (in a determination step ST4).

After the air quality condition of the sample gas has been determined by the determiner 55, the outputter 56 outputs the decision made by the determiner 55 to the display device 57 (in an output step ST5). In other words, the output step ST5 includes outputting the decision made in the determination step. This allows the user of the air quality determination system 1 to check the air quality condition of the sample gas by confirming the information displayed on the display device 57. Alternatively, the output step ST5 may include outputting the decision made in the determination step to an external system, thus allowing the external system to use the decision made in the determination step.

The variation in the electrical characteristic value due to the temperature is relatively significant compared to the variation in the electrical characteristic value in reaction to the molecules to detect, and therefore, the effect of the temperature in the environment surrounding the sensitive unit 2 on the decision is non-negligible. The air quality determination system 1 according to this embodiment uses sensitive elements Ax made of a sensitive material suitable for causing the temperature variation pattern to the sensitive unit 2 to amplify the variation in the electrical characteristic value in reaction to the molecules. This enables determining the air quality condition more accurately. In addition, the air quality determination system 1 according to this embodiment acquires a variation pattern in the electrical characteristic value with the variation in the electrical characteristic value due to the temperature reduced by calculating the difference between the variation pattern in the electrical characteristic value in reaction to the molecules to detect and the variation pattern in the electrical characteristic value in reaction to the standard gas. This allows the air quality condition to be determined more accurately based on this variation pattern.

(3) Variations

Note that the embodiment described above is only an exemplary one of various embodiments of the present disclosure and should not be construed as limiting. Rather, the exemplary embodiment may be readily modified in various manners depending on a design choice or any other factor without departing from the scope of the present disclosure. Also, the functions of the air quality determination system 1 may also be implemented as, for example, an air quality determination method, a computer program, or a non-transitory storage medium on which the program is stored. An air quality determination method according to an aspect includes an exposure step, a temperature variation step, and a determination step. The exposure step includes exposing a sensitive unit 2 to a sample gas. The sensitive unit 2 includes an organic composition 21 and conductive particles 22 dispersed in the organic composition 21. An electrical characteristic value of the sensitive unit 2 changes in reaction to one or more types of molecules, to which the sensitive unit 2 has sensitivity. The temperature variation step includes causing the temperature of the sensitive unit 2 exposed to the sample gas to vary in a temperature variation pattern including at least one temperature rising period UT1 and at least one temperature falling period DT1. The temperature rising period UT1 is a period in which the temperature of the sensitive unit 2 rises. The temperature falling period DT1 is a period in which the temperature of the sensitive unit 2 falls. The determination step includes determining the air quality condition of the sample gas based on a variation pattern of the electrical characteristic value with the temperature of the sensitive unit 2 exposed to the sample gas caused to vary in the temperature variation pattern. A (computer) program according to another aspect is designed to cause a computer system to perform the exposure step, the temperature variation step, and the determination step.

Next, variations of the exemplary embodiment will be enumerated one after another. Note that the variations to be described below may be adopted in combination as appropriate.

The air quality determination system 1 according to the present disclosure includes a computer system in the processor 50 thereof, for example. The computer system may include a processor and a memory as principal hardware components thereof. The functions of the air quality determination system 1 according to the present disclosure may be performed by making the processor execute a program stored in the memory of the computer system. The program may be stored in advance in the memory of the computer system. Alternatively, the program may also be downloaded through a telecommunications line or be distributed after having been recorded in some non-transitory storage medium such as a memory card, an optical disc, or a hard disk drive, any of which is readable for the computer system. The processor of the computer system may be made up of a single or a plurality of electronic circuits including a semiconductor integrated circuit (IC) or a large-scale integrated circuit (LSI). As used herein, the "integrated circuit" such as an IC or an LSI is called by a different name depending on the degree of integration thereof. Examples of the integrated circuits include a system LSI, a very-large-scale integrated circuit (VLSI), and an ultra-large-scale integrated circuit (ULSI). Optionally, a field-programmable gate array (FPGA) to be programmed after an LSI has been fabricated or a reconfigurable logic device allowing the connections or circuit sections inside of an LSI to be reconfigured may also be adopted as the processor. Those electronic circuits may be either integrated together on a single chip or distributed on multiple chips, whichever is appropriate. Those multiple chips may be aggregated together in a single device or distributed in multiple devices without limitation. As used herein, the "computer system" includes a microcontroller including one or more processors and one or more memories. Thus, the microcontroller may also be implemented as a single or a plurality of electronic circuits including a semiconductor integrated circuit or a large-scale integrated circuit.

Also, in the embodiment described above, the plurality of functions of the air quality determination system 1 are integrated together in a single housing. However, this is not an essential configuration for the air quality determination system 1. Alternatively, those constituent elements of the air quality determination system 1 may be distributed in multiple different housings. Still alternatively, at least some functions of the air quality determination system 1 (e.g., some functions of the air quality determination system 1) may be implemented as a cloud computing system as well.

(3.1) First Variation

In an air quality determination system 1 according to a first variation, the determiner 55 determines the air quality condition of the sample gas based on a difference between a first variation pattern and a second variation pattern, which is a difference from the exemplary embodiment described above. Specifically, the first variation pattern is a variation pattern (output data PS) in the electrical characteristic value in a state where the temperature of the sensitive unit 2 exposed to the sample gas is caused to vary in the temperature variation pattern. The second variation pattern is a variation pattern (standard output data PS0) in the electrical characteristic value of the sensitive unit 2 in a state where the temperature of the sensitive unit 2 exposed to the sample gas is caused to vary in the temperature variation pattern. The first variation is the same as the exemplary embodiment described above except the configuration of the determiner 55. Thus, in the following description, any constituent element of this first variation, having the same function as a counterpart of the embodiment described above, will be designated by the same reference numeral as that counterpart's, and description thereof will be omitted herein.

On acquiring the pulse outputs PL1-PL16 from the sixteen sensitive elements A1-A16 with the temperature of the sensitive unit 2 exposed to the sample gas caused to vary in the temperature variation pattern, the acquirer 53 obtains output data (as the first variation pattern) by connecting the pulse outputs PL1-PL16 to each other. The storage device 52 stores in advance the standard output data PS0 (as the second variation pattern) collected when the temperature of the sensitive unit 2 is caused to vary in multiple different temperature variation patterns with the sensitive unit 2 exposed to the standard gas. The acquirer 53 acquires, based on the result of detection of the temperature acquired from the temperature sensor 4, the standard output data PS0 corresponding to the temperature variation pattern of the sensitive unit 2 from the storage device 52, obtains differential data representing the difference between the output data of the first variation pattern and the standard output data PS0 of the second variation pattern, and outputs the differential data to the determiner 55.

In the first variation, the learned model MD1 that has been generated using the differential data as the learning data is stored in the storage device 52. This allows the determiner 55 to determine the air quality condition of the sample gas by inputting the differential data, representing the difference between the output data of the first variation pattern and the standard output data PS0 of the second variation pattern, to the learned model MD1.

Figure 11:
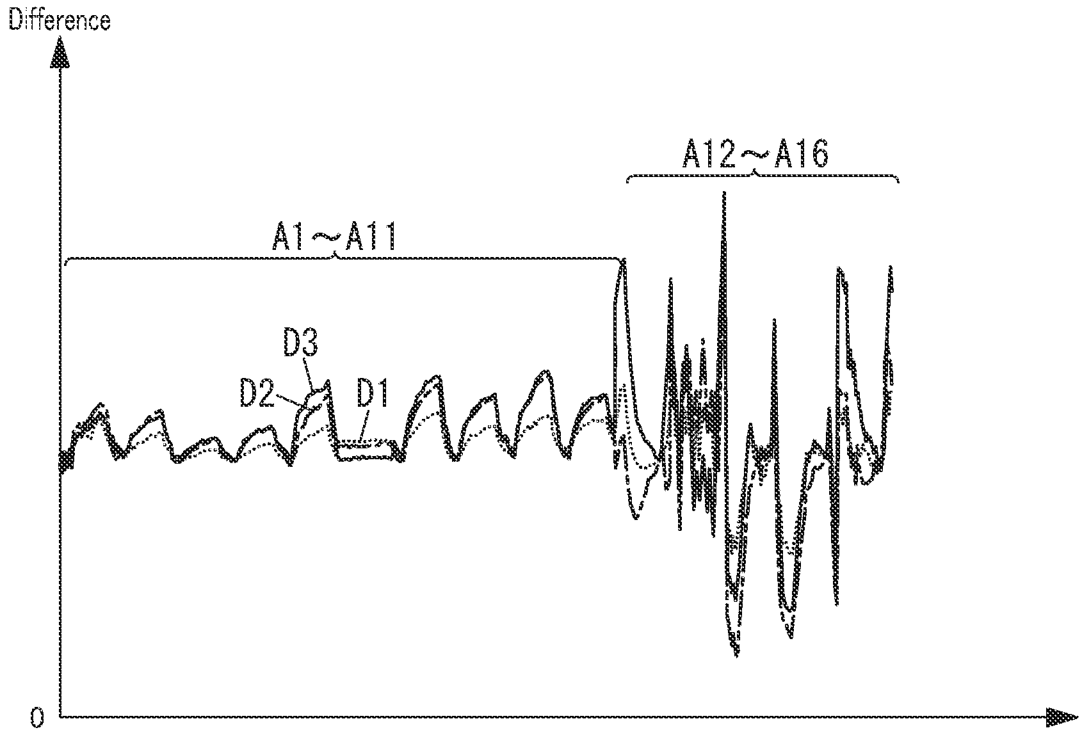
FIG. 11 shows differential data collected in a situation where the temperature of a sensitive unit of an air quality determination system according to a first variation was caused to vary within a temperature range from 25° C. to 50° C.
Figure 12:
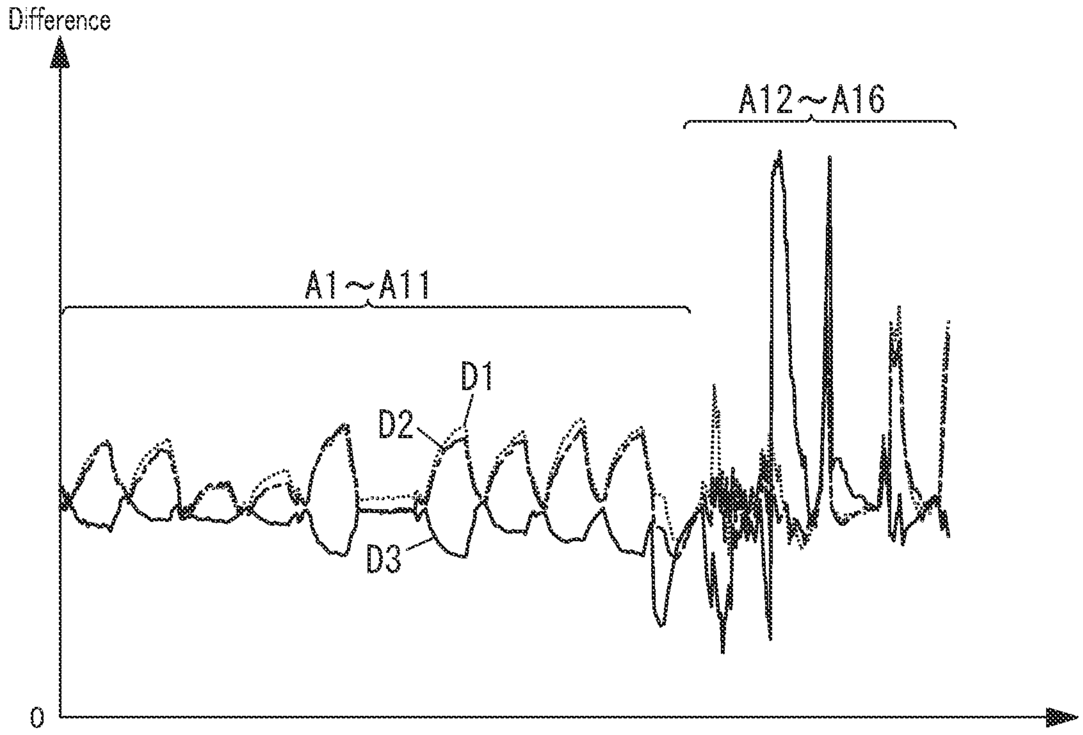
FIG. 12 shows differential data collected in a situation where the temperature of the sensitive unit of the air quality determination system according to the first variation was caused to vary within a temperature range from 0° C. to 25° C.
Figure 13:
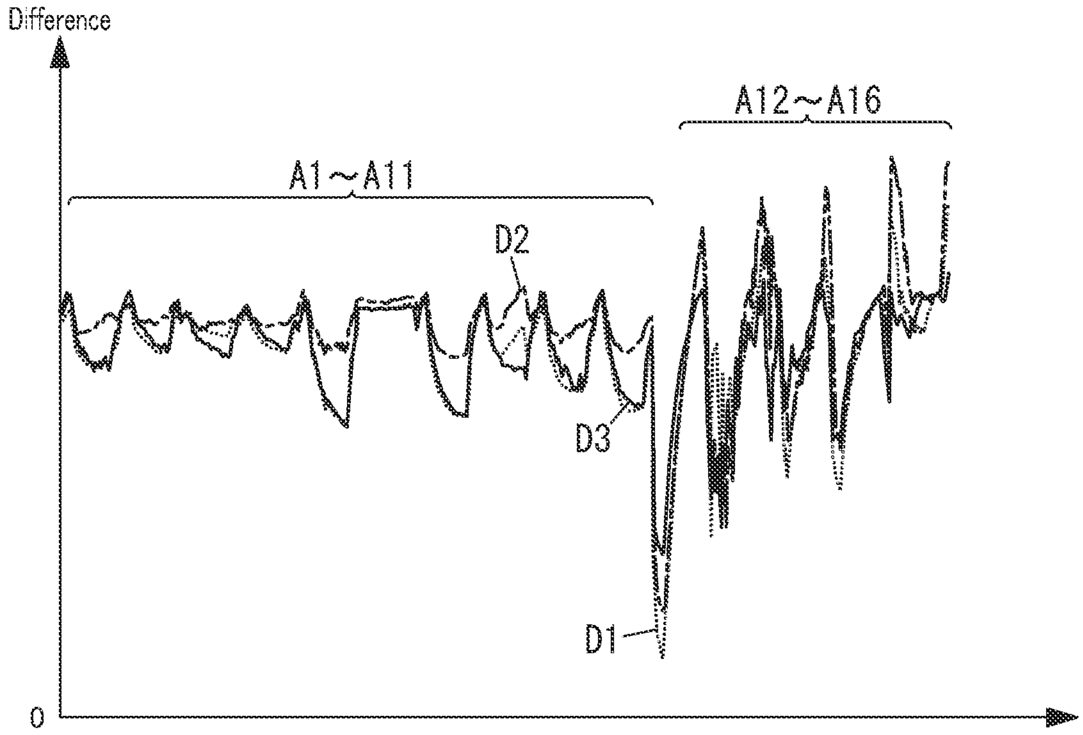
FIG. 13 shows differential data collected in a situation where the temperature of the sensitive unit of the air quality determination system according to the first variation was caused to vary within a temperature range from −20° C. to 5° C.

Exemplary results of calculation of the differential data are shown in FIGS. 11-13. Specifically, the differential data D1-D3 shown in FIG. 11 is calculated based on the output data PS11-PS13 and the standard output data PS0 in a state where the temperature of the sensitive unit 2 is caused to vary within a temperature range equal to or higher than 25° C. and equal to or lower than 50° C. The differential data D1-D3 shown in FIG. 12 is calculated based on the output data PS11-PS13 and the standard output data PS0 in a state where the temperature of the sensitive unit 2 is caused to vary within a temperature range equal to or higher than 0° C. and equal to or lower than 25° C. The differential data D1-D3 shown in FIG. 13 is calculated based on the output data PS11-PS13 and the standard output data PS0 in a state where the temperature of the sensitive unit 2 is caused to vary within a temperature range equal to or higher than −20° C. and equal to or lower than 5° C.

In FIGS. 11-13, the differential data D1 is obtained by subtracting the standard output data PS0 from the output data PS11 in a situation where the sensitive unit 2 is exposed to a sample gas including 2 ppm of benzaldehyde. Also, in FIGS. 11-13, the differential data D2 is obtained by subtracting the standard output data PS0 from the output data PS12 in a situation where the sensitive unit 2 is exposed to a sample gas including 2 ppm of nonanal. In FIGS. 11-13, the differential data D3 is obtained by subtracting the standard output data PS0 from the output data PS13 in a situation where the sensitive unit 2 is exposed to a sample gas including 2 ppm of pyrrole.

In the first variation, the differential data D1-D3 is obtained by subtracting the standard output data PS0 from the output data in a situation where the sensitive unit 2 is exposed to a sample gas including odor molecules. The variation components caused to the resistance value due to the temperature variation of the sensitive unit 2 have been removed from the differential data D1-D3 and only the variation components caused to the resistance value due to the presence of the odor molecules are left in the differential data D1-D3. This allows the determiner 55 to determine, based on the differential data D1-D3, the air quality condition of the sample gas accurately.

Note that in the differential data D1-D3, the differential value of a pulse signal corresponding to a negative characteristic sensitive element (namely, each of the sensitive elements A1-A11) increases in a temperature range equal to or higher than −20° C. and equal to or lower than 10° C. This allows, as for the temperature range equal to or higher than −20° C. and equal to or lower than 10° C., the determiner 55 to accurately determine the air quality of the sample gas based on the differential value of a pulse signal corresponding to a negative characteristic sensitive element (namely, each of the sensitive elements A1-A11) in the differential data D1-D3.

Also, in the differential data D1-D3, the differential value of a pulse signal corresponding to a positive characteristic sensitive element (namely, each of the sensitive elements A12-A16) increases in a temperature range equal to or higher than 20° C. and equal to or lower than 50° C. This allows, as for the temperature range equal to or higher than 20° C. and equal to or lower than 50° C., the determiner 55 to accurately determine the air quality of the sample gas based on the differential value of a pulse signal corresponding to a positive characteristic sensitive element (namely, each of the sensitive elements A12-A16) in the differential data D1-D3.

(3.2) Second Variation

Next, an air quality determination system 1 according to a second variation will be described with reference to FIGS. 14 and 15.

In the second variation, the sensitive unit 2 includes a plurality of sensitive modules, which is a difference from the exemplary embodiment described above. In the other respects, the second variation is the same as the exemplary embodiment. Thus, in the following description, any constituent element of this second variation, having the same function as a counterpart of the embodiment described above, will be designated by the same reference numeral as that counterpart's, and description thereof will be omitted herein.

The sensitive unit 2 includes a plurality of sensitive modules, which are arranged in the housing space 11 of the sensor housing chamber 10. In FIG. 14, the sensitive unit 2 includes three sensitive modules 2A-2C. In addition, the air quality determination system 1 according to the second variation includes a temperature control element 3 for controlling the respective temperatures of the three sensitive modules 2A-2C on an individual basis.

In this case, the air quality determination method includes a temperature control step, an acquisition step, and a determination step. The temperature control step includes controlling temperatures of the plurality of sensitive modules 2A-2C exposed to a sample gas in a predetermined measurement period to cause the temperature of each of the plurality of sensitive modules 2A-2C to vary in a temperature variation pattern including at least one temperature rising period and at least one temperature falling period. The acquisition step includes acquiring the electrical characteristic value of each of the plurality of sensitive modules 2A-2C exposed to the sample gas. The determination step includes determining, using a learned model to determine an air quality condition of the sample gas, the air quality condition of the sample gas based on a variation in the electrical characteristic value of each of the plurality of sensitive modules 2A-2C.

Also, the air quality determination system 1 according to the second variation includes the plurality of sensitive modules 2A-2C, a sensor housing chamber 10 serving as an exposure unit, a temperature control element 3, a temperature controller 51, an acquirer 53, a determiner 55, and an outputter 56. An electrical characteristic value of each of the plurality of sensitive modules 2A-2C changes in reaction to one or more types of molecules. The exposure unit exposes the plurality of sensitive modules 2A-2C to a sample gas in a predetermined measurement period. The temperature control element 3 heats and/or cools the plurality of sensitive modules 2A-2C. The controller 51 controls the temperature control element 3 to cause the temperature of each of the plurality of sensitive modules 2A-2C exposed to the sample gas in the predetermined measurement period to vary in a temperature variation pattern including at least one temperature rising period in which the temperature of the sensitive module 2A-2C rises and at least one temperature falling period in which the temperature of the sensitive module 2A-2C falls. The acquirer 53 acquires the electrical characteristic values of the plurality of sensitive modules 2A-2C in the predetermined measurement period. The determiner 55 determines, using a learned model MD1 to determine an air quality condition of the sample gas, the air quality condition of the sample gas based on variations in the electrical characteristic values of the plurality of sensitive modules 2A-2C. The outputter 56 outputs a decision made by the determiner 55.

In this variation, each of the plurality of sensitive modules 2A-2C includes: a plurality of sensitive elements having mutually different sensitivities; and a board on which the plurality of sensitive elements are formed. The respective boards of the plurality of sensitive modules 2A-2C are mutually different boards. In other words, the plurality of sensitive modules 2A-2C includes at least a first sensitive module and a second sensitive module and the board included in the first sensitive module and the board included in the second sensitive module are two different boards. Specifically, the sensitive module 2A includes a board 20A on which the plurality of sensitive elements A1-A16 are provided. The sensitive module 2B includes a board 20B on which the plurality of sensitive elements A1-A16 are provided. The sensitive module 2C includes a board 20C on which the plurality of sensitive elements A1-A16 are provided. Note that each of these boards 20A-20C is provided with the temperature control element 3 and the temperature of each of the sensitive modules 2A-2C is controlled by the temperature control element 3 provided for the sensitive module 2A-2C on an individual basis.

Figure 14:
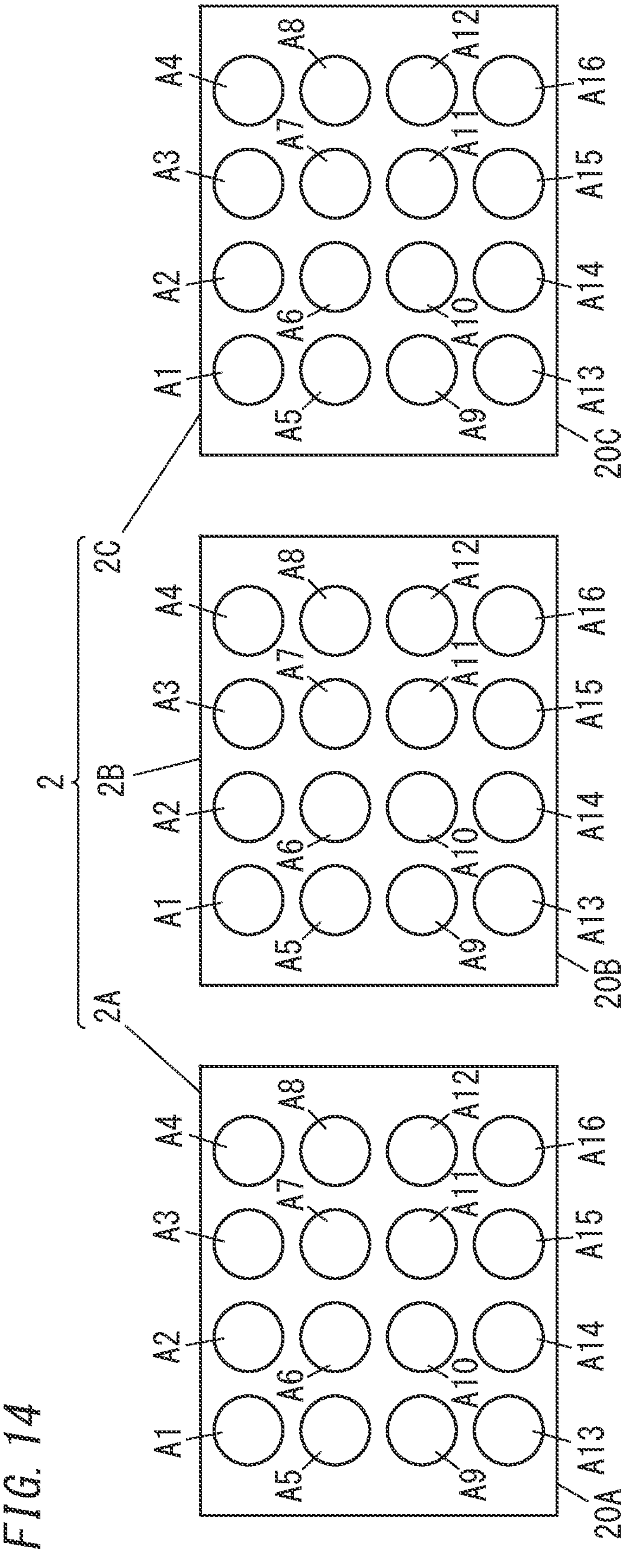
FIG. 14 is a schematic plan view of a plurality of sensitive modules included in an air quality determination system according to a second variation.
Figure 15:
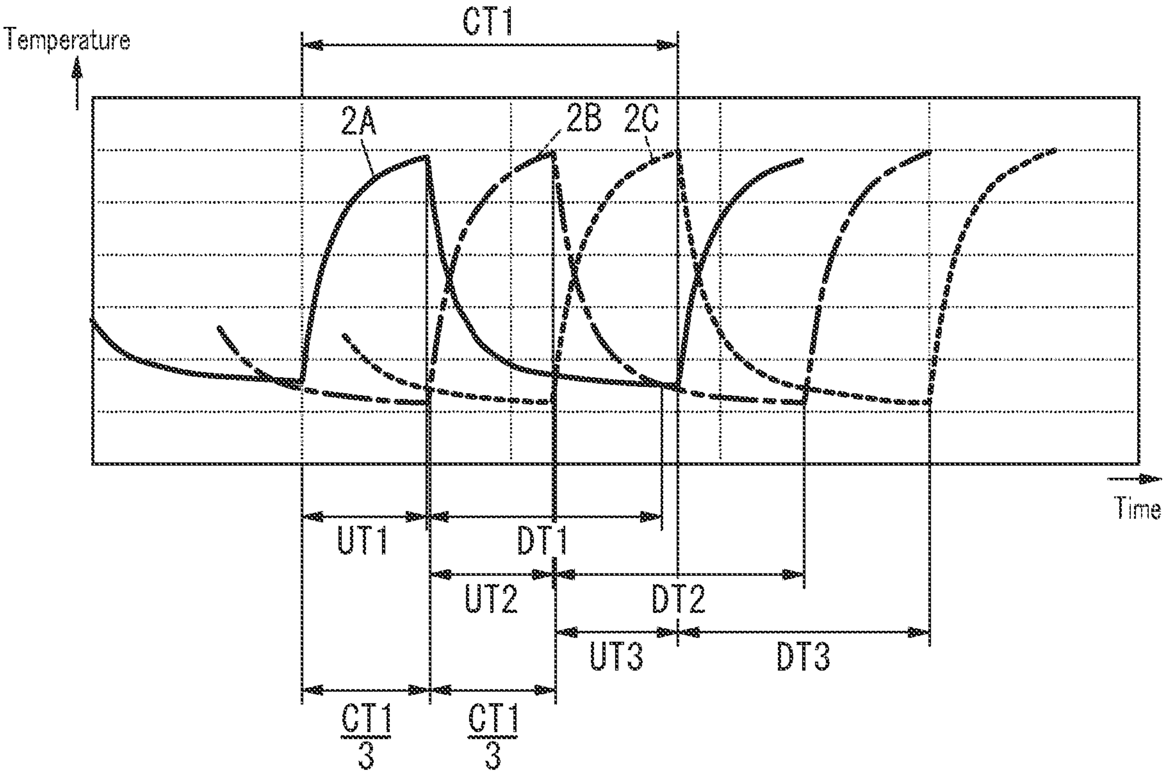
FIG. 15 is a graph how the temperatures of the plurality of sensitive modules included in the air quality determination system according to the second variation change with time.

Furthermore, in the example shown in FIG. 14, each of the plurality of (e.g., three in the second variation) sensitive modules 2A-2C includes the same combination of sensitive elements. Specifically, each of the plurality of sensitive modules 2A-2C includes the same combination of sixteen sensitive elements A1-A16. The temperature control step includes causing the temperature of the plurality of sensitive modules 2A-2C to vary in a temperature variation pattern including at least one temperature rising period and at least one temperature falling period. In this variation, at least one of the temperature rising and falling periods of each of the plurality of sensitive modules 2A-2C is temporally shifted from the counterpart of any other one of the plurality of sensitive modules 2A-2C. In other words, the plurality of sensitive modules 2A-2C includes at least a first sensitive module and a second sensitive module and the temperature control step includes temporally shifting at least one of the temperature rising and falling periods of the first sensitive module from the counterpart of the second sensitive module. FIG. 15 is a graph showing the respective temperature variations of the three sensitive modules 2A-2C. The temperature control step includes causing the temperature of each of the three sensitive modules 2A-2C to vary in a cycle time CT1 including a temperature rising period UT1 and a temperature falling period DT1. In addition, the temperature control step also includes causing the respective temperatures of the three sensitive modules 2A-2C to vary at a regular interval corresponding to a time difference (CT1/3) that is one third of one cycle time CT1, including the temperature rising period UT1 and the temperature falling period DT1. This enables determining, in the determination step, the air quality condition every time a time corresponding to the time difference (CT1/3) passes. Thus, although it takes one full cycle time CT1 to have the determination done if only one sensitive module is provided, providing n sensitive modules (where n is an integer equal to or greater than two) enables shortening the time it takes to have the determination step done to one-$n^{th}$ of one cycle time CT1 (=CT1/n).

Figure 16:
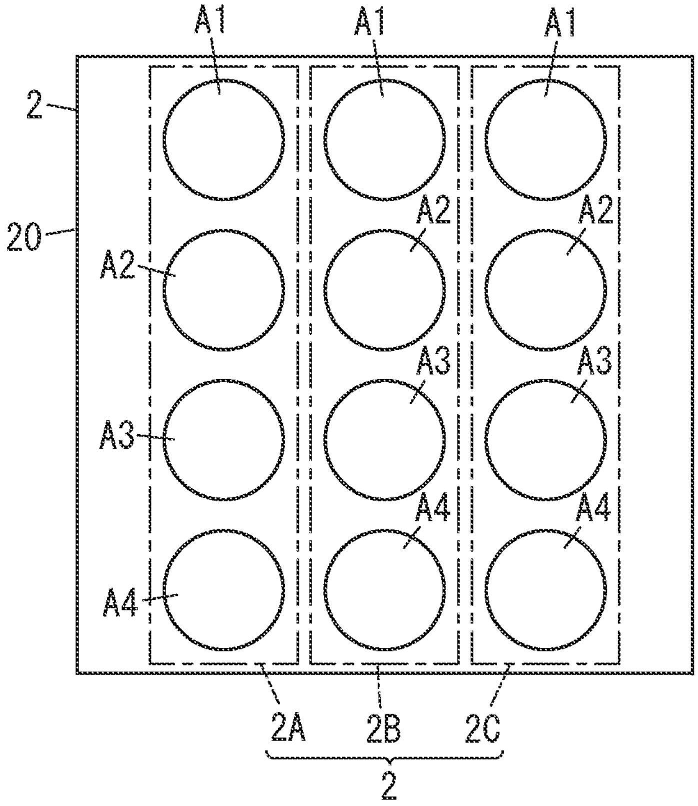
FIG. 16 is a schematic plan view of a plurality of sensitive modules included in the air quality determination system according to the second variation.
Figure 17:
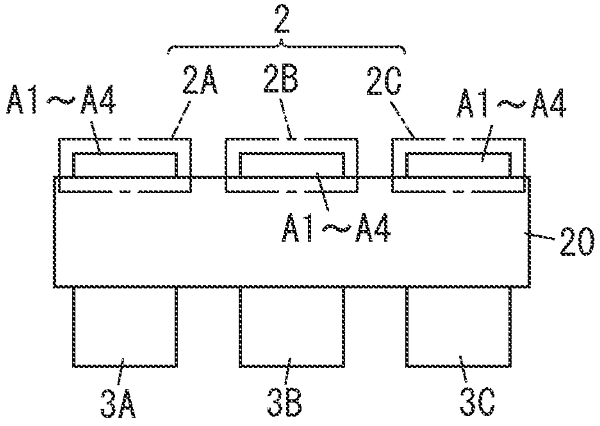
FIG. 17 is a side view of a sensitive unit included in the air quality determination system according to the second variation.

Note that the plurality of sensitive modules 2A-2C do not have to be provided on three different boards 20A-20C. Alternatively, the plurality of (e.g., three) sensitive modules 2A-2C may also be provided on a single board 20 as shown in FIGS. 16 and 17. Specifically, each of the plurality of sensitive modules 2A-2C includes a plurality of sensitive elements A1-A4 having mutually different sensitivities and the plurality of sensitive elements A1-A4 included in each of the plurality of sensitive modules 2A-2C are formed on the same board 20. In other words, the plurality of sensitive modules 2A-2C includes at least the first sensitive module and the second sensitive module. Each of the first sensitive module and the second sensitive module includes a plurality of sensitive elements A1-A4 having mutually different sensitivities. In addition, the plurality of sensitive elements A1-A4 included in the first sensitive module and the plurality of sensitive elements A1-A4 included in the second sensitive module are all formed on a single board 20.

In this variation, on a first surface of the board 20, the sensitive elements A1-A4 of the sensitive module 2A, the sensitive elements A1-A4 of the sensitive module 2B, and the sensitive elements A1-A4 of the sensitive module 2C are arranged in three columns. On the other hand, on a second surface (i.e., the reverse surface opposite from the first surface) of the board 20, a temperature control element 3A for causing the temperature of the sensitive module 2A to vary is disposed on the reverse of the region where the sensitive elements A1-A4 of the sensitive module 2A are arranged. In addition, on the second surface of the board 20, a temperature control element 3B for causing the temperature of the sensitive module 2B to vary is disposed on the reverse of the region where the sensitive elements A1-A4 of the sensitive module 2B are arranged. Furthermore, on the second surface of the board 20, a temperature control element 3C for causing the temperature of the sensitive module 2C to vary is disposed on the reverse of the region where the sensitive elements A1-A4 of the sensitive module 2C are arranged.

As can be seen, on the second surface of the board 20, provided are the temperature control elements 3A-3C for causing the respective temperatures of the sensitive modules 2A-2C to vary. This enables controlling the temperatures of the sensitive modules 2A-2B on an individual basis.

Note that in this second variation, the sensitive unit 2 includes the three sensitive modules 2A-2C. However, the number of the sensitive modules provided does not have to be three. Rather, the sensitive unit 2 only needs to include a plurality of sensitive modules. The number of the sensitive modules provided may also be two or even four or more.

Figure 18:
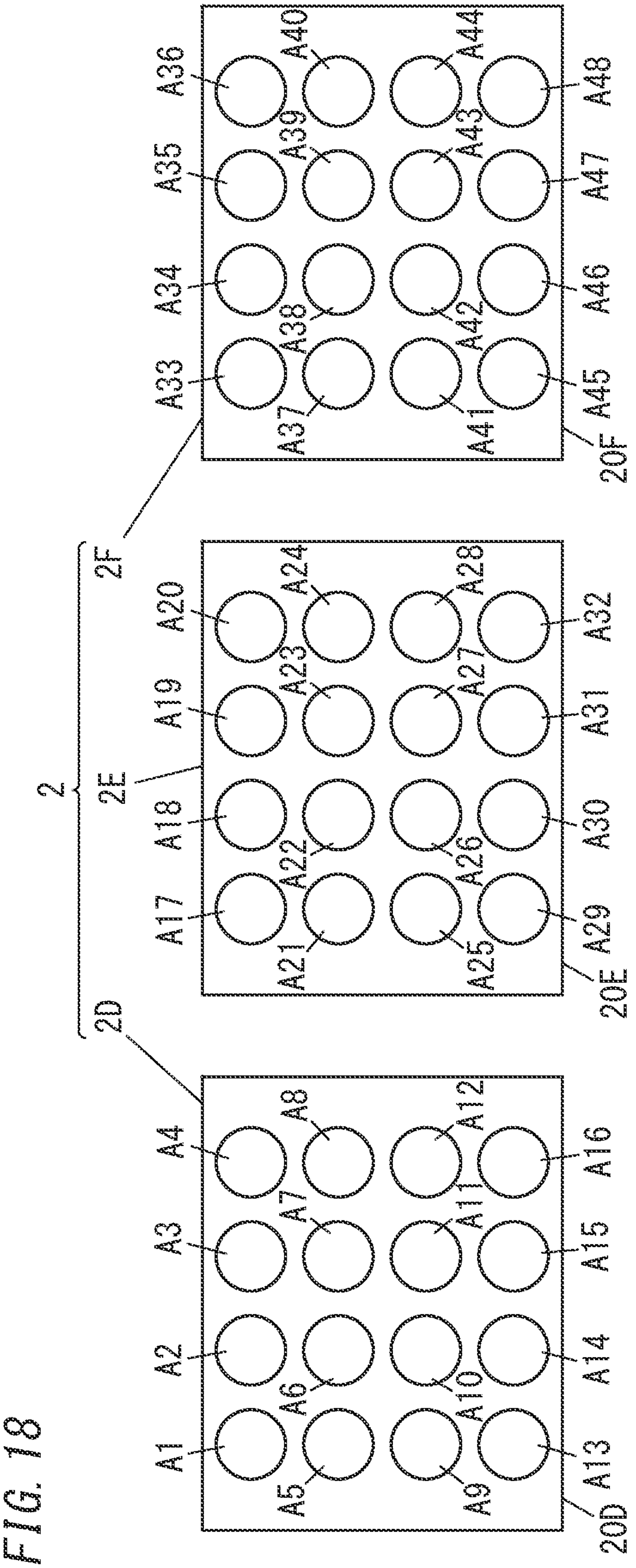
FIG. 18 is a schematic plan view of a plurality of sensitive modules included in the air quality determination system according to the second variation.

Optionally, in the second variation, the combination of sensitive elements included in each of the plurality of sensitive modules may be different from the combination of sensitive elements included in any other one of the plurality of sensitive modules. In other words, if the plurality of sensitive modules includes at least a first sensitive module and a second sensitive module, the combination of the sensitive elements included in the first sensitive module may be different from the combination of the sensitive elements included in the second sensitive module. In this case, not all of the sensitive elements included in the first sensitive module have to be different from the sensitive elements included in the second sensitive module but at least one of the sensitive elements included in the first sensitive module needs to be different from any of the sensitive elements included in the second sensitive module. FIG. 18 illustrates an example of three sensitive modules 2D-2F included in the sensitive unit 2. The sensitive module 2D includes sixteen sensitive elements A1-A16 and a board 20D on which the sixteen sensitive elements A1-A16 are arranged. The sensitive module 2E includes sixteen sensitive elements Al 7-A32 and a board 20E on which the sixteen sensitive elements A1 7-A32 are arranged. The sensitive module 2F includes sixteen sensitive elements A33-A48 and a board 20F on which the sixteen sensitive elements A33-A48 are arranged. In addition, the air quality determination system 1 further includes a temperature control element 3 for controlling the respective temperatures of the sensitive modules 2D-2F on an individual basis.

In this variation, the combination of sensitive elements included in each of the plurality of sensitive modules 2D-2F is different from the combination of sensitive elements included in any other one of the plurality of sensitive modules 2D-2F. Thus, each of the plurality of sensitive modules 2D-2F preferably includes an appropriate combination of sensitive elements suitable for its purpose. Examples of the intended use of the plurality of sensitive modules 2D-2F include determining the odor of a gas (such as breath) emitted from a human body, making quality control of a food by determining either whether the food emits any gas indicating its putrefaction or the species of the gas if the answer is YES, determining the air quality condition inside a room, determining whether or not there is any gas produced by a fire, any gas emitted from an explosive or a drug, or any poisonous gas. Arranging a plurality of sensitive modules suitable for multiple different purposes in the housing space 11 allows the air quality determination system 1 to perform multiple types of determination processing suitable for those purposes.

Since the plurality of sensitive modules 2D-2F include respectively different combinations of sensitive elements, the temperature variation patterns for causing the temperatures of the plurality of sensitive modules 2D-2F to vary may be the same as each other or different from each other, whichever is appropriate. For example, the temperature variation patterns for causing the temperatures of the plurality of sensitive modules 2D-2F to vary may be temporally shifted from each other or synchronized with each other, whichever is appropriate.

In other words, if the plurality of sensitive modules 2D-2F includes at least a first sensitive module and a second sensitive module, the first temperature variation pattern for causing the temperature of the first sensitive module to vary and the second temperature variation pattern for causing the temperature of the second sensitive module to vary may be the same as each other or different from each other, whichever is appropriate. As used herein, if the first and second temperature variation patterns are the same as each other, it means that the temperature rising and falling periods of the first temperature variation pattern and the temperature rising and falling periods of the second temperature variation pattern agree with each other and cause the temperature to vary within the same range. On the other hand, as used herein, if the first and second temperature variation patterns are different from each other, at least one of the temperature rising and falling periods of the first temperature variation pattern may be different from the counterpart of the second temperature variation pattern or the temperature may vary within a different range in at least one of the temperature rising and falling periods of the first temperature variation pattern from in the counterpart of the second temperature variation pattern. Alternatively, as used herein, if the first and second temperature variation patterns are different from each other, at least one of the temperature rising and falling periods of the first temperature variation pattern may be different from the counterpart of the second temperature variation pattern and the temperature may vary within a different range in at least one of the temperature rising and falling periods of the first temperature variation pattern from in the counterpart of the second temperature variation pattern.

(3.3) Other Variations

In the air quality determination system 1 according to the exemplary embodiment described above, the temperature control element 3 is implemented as the electrothermal element 31. However, this is only an example and should not be construed as limiting. Alternatively, the temperature control element 3 may also be a Peltier element that may both raise and lower the temperature of the sensitive unit 2. Alternatively, the temperature control element 3 may include at least one of a Peltier element or an electrothermal element. Furthermore, in the exemplary embodiment described above, the temperature control element 3 is the electrothermal element 31, thus enabling downsizing the temperature control element 3 and cutting down the power consumption compared to a situation where a Peltier element is used as the temperature control element 3.

Also, in the air quality determination system 1 according to the exemplary embodiment described above, the sensitive unit 2 includes sixteen sensitive elements Ax. However, the number of the sensitive elements Ax provided may be changed as appropriate. The sensitive unit 2 includes both negative characteristic sensitive elements and positive characteristic sensitive elements. However, this is only an example and should not be construed as limiting. Alternatively, the sensitive unit 2 may include only negative characteristic sensitive elements or only positive characteristic sensitive elements. Furthermore, in the air quality determination system 1 according to the exemplary embodiment described above, the sixteen sensitive elements Ax are arranged in four columns and four rows. However, the plurality of sensitive elements Ax do not have to be arranged in the arrangement pattern described for the exemplary embodiment. Alternatively, the plurality of sensitive elements may also be arranged in line. Still alternatively, the plurality of sensitive elements may also be arranged at intervals to form a single circular pattern or a plurality of concentric circular pattern.

Furthermore, in the air quality determination system 1 according to the exemplary embodiment described above, the temperature controller 51 controls the temperature control element 3 to cause the temperatures of the sensitive elements A1-A16 to vary in the same temperature variation pattern. Alternatively, the respective temperatures of the sensitive elements A1-A16 may also be caused to vary in multiple different temperature variation patterns. For example, the sensitive elements A1-A11, of which the sensitivity to the odor molecules increases within the temperature range equal to or higher than −20° C. and equal to or lower than 25° C., preferably have their temperature varied within the temperature range equal to or higher than −20° C. and equal to or lower than 25° C. On the other hand, the sensitive elements A12-A16, of which the sensitivity to the odor molecules increases within the temperature range equal to or higher than 20° C. and equal to or lower than 50° C., preferably have their temperature varied within the temperature range equal to or higher than 20° C. and equal to or lower than 50° C.

In the air quality determination method described above, the acquisition step may include acquiring the electrical characteristic value of the sensitive unit 2 via a network.

In the air quality determination system 1 according to the exemplary embodiment described above, the learned model MD1 is stored in the storage device 52 of the air quality determination system 1. Alternatively, the air quality determination system 1 may determine the air quality condition using a learned model MD1 located on a cloud computing system. Specifically, in that case, the determiner 55 of the air quality determination system 1 inputs, to the learned model on the cloud computing system, output data representing a variation pattern of the electrical characteristic value (resistance value) in a state where the temperature of the sensitive unit 2 exposed to the sample gas is caused to vary in the temperature variation pattern described above. That is to say, the learned model on the cloud computing system performs determination processing using the electrical characteristic value of the sensitive unit 2, which has been acquired via a network, and transmits the decision to the determiner 55. In this manner, the determiner 55 may determine the air quality condition of the sample gas by acquiring the decision from the learned model on the cloud computing system.

Alternatively, a server having the function of the determination module 5 may acquire the electrical characteristic value from the sensitive unit 2 via a network and the determiner 55 may perform the determination processing using the electrical characteristic value of the sensitive unit 2 thus acquired. In that case, the server having the function of the determination module 5 may perform the determination processing by acquiring the electrical characteristic value of the sensitive unit 2 in real time. Alternatively, the server may perform the determination processing by acquiring time series data of the electrical characteristic value of the sensitive unit 2 from, for example, a data server that stores the time series data of the electrical characteristic value of the sensitive unit 2.

(Recapitulation)

As can be seen from the foregoing description, an air quality determination method according to a first aspect is a method for determining an air quality using a sensitive unit (2), of which an electrical characteristic value changes in reaction to one or more types of molecules. The air quality determination method includes a temperature control step, an acquisition step, a determination step, and an output step. The temperature control step includes controlling a temperature of the sensitive unit (2) exposed to a sample gas in a predetermined measurement period to cause the temperature of the sensitive unit (2) to vary in a temperature variation pattern including at least one temperature rising period in which the temperature of the sensitive unit (2) rises and at least one temperature falling period in which the temperature of the sensitive unit (2) falls. The acquisition step includes acquiring the electrical characteristic value of the sensitive unit (2) exposed to the sample gas. The determination step includes determining, using a learned model to determine an air quality condition of the sample gas, the air quality condition of the sample gas based on a variation in the electrical characteristic value. The output step includes outputting a decision made in the determination step.

According to this aspect, when the electrical characteristic value of the sensitive unit (2) changes in response to a molecule to which the sensitive unit (2) has sensitivity, the variation pattern of the electrical characteristic value in the temperature rising period and the temperature falling period changes from a variation pattern in a state where there are no molecules to which the sensitive unit (2) has sensitivity. This enables determining, in the determination step, the air quality condition of the sample gas based on a variation in the electrical characteristic value in the temperature rising period and the temperature falling period. Consequently, this enables reducing the chances of determining the air quality condition erroneously due to variation components caused by the temperature, thereby reducing the chances of causing a decline in the accuracy of the air quality condition determined.

In an air quality determination method according to a second aspect, which may be implemented in conjunction with the first aspect, the determination step includes determining the air quality condition of the sample gas based on a difference between a first variation pattern and a second variation pattern. The first variation pattern is a variation pattern of the electrical characteristic value in a state where the temperature of the sensitive unit (2) exposed to the sample gas is caused to vary in the temperature variation pattern. The second variation pattern is a variation pattern of the electrical characteristic value in a state where the temperature of the sensitive unit (2) exposed to a standard gas is caused to vary in the temperature variation pattern.

This aspect enables, by calculating the difference between the first variation pattern and the second variation pattern, reducing the variation components to be caused in the electrical characteristic value when the temperature of the sensitive unit (2) is caused to vary in the temperature variation pattern. This enables determining, in the determination step, the air quality condition of the sample gas accurately based on the difference between the first variation pattern and the second variation pattern.

In an air quality determination method according to a third aspect, which may be implemented in conjunction with the first or second aspect, the sensitive unit (2) includes a plurality of sensitive elements (Ax) having mutually different sensitivities. The determination step includes determining the air quality condition of the sample gas based on respective variation patterns of the electrical characteristic value of the plurality of sensitive elements (Ax) in a state where temperatures of the plurality of sensitive elements (Ax) exposed to the sample gas are caused to vary in the temperature variation pattern.

According to this aspect, the air quality condition of the sample gas is determined based on the variation patterns in the electrical characteristic value of a plurality of sensitive elements (Ax). This enables determining the air quality of a sample gas including more types of molecules than in a situation where only one sensitive element (Ax) is provided.

In an air quality determination method according to a fourth aspect, which may be implemented in conjunction with any one of the first to third aspects, the sensitive unit (2) includes a negative characteristic sensitive element (A1-A11) having a negative resistance coefficient in a temperature range equal to or higher than −20° C. and equal to or lower than 50° C.

This aspect enables determining the air quality condition of a sample gas based on a variation pattern in the electrical characteristic value of a sensitive unit (2) including a negative characteristic sensitive element (A1-A11).

In an air quality determination method according to a fifth aspect, which may be implemented in conjunction with the fourth aspect, the temperature control step includes causing a temperature of the negative characteristic sensitive element (A1-A11) to vary in the temperature variation pattern including a temperature rising period in which the temperature of the negative characteristic sensitive element (A1-A11) is raised within a temperature range equal to or higher than −20° C. and equal to or lower than 20° C. and a temperature falling period in which the temperature of the negative characteristic sensitive element (A1-A11) is lowered within the temperature range equal to or higher than −20° C. and equal to or lower than 20° C. This aspect enables determining the air quality condition of a sample gas based on a variation pattern in the electrical characteristic value when the temperature of a negative characteristic sensitive element (A1-A11) is raised and lowered within the temperature range equal to or higher than −20° C. and equal to or lower than 20° C.

In an air quality determination method according to a sixth aspect, which may be implemented in conjunction with the fourth or fifth aspect, the negative characteristic sensitive element (A1-A11) includes an organic composition (21) and conductive particles (22) dispersed in the organic composition (21). The organic composition (21) included in the negative characteristic sensitive element (A1-A11) has siloxane on a main chain thereof and has a methyl group on a side chain thereof.

This aspect enables determining the air quality condition of a sample gas based on a variation pattern in the electrical characteristic value of a sensitive unit (2) including a negative characteristic sensitive element (A1-A11).

In an air quality determination method according to a seventh aspect, which may be implemented in conjunction with any one of the first to sixth aspects, the sensitive unit (2) includes a positive characteristic sensitive element (A12-A16) having a positive resistance coefficient in a temperature range equal to or higher than −20° C. and equal to or lower than 50° C.

This aspect enables determining the air quality condition of a sample gas based on a variation pattern in the electrical characteristic value of a sensitive unit (2) including a positive characteristic sensitive element (A12-A16).

In an air quality determination method according to an eighth aspect, which may be implemented in conjunction with the seventh aspect, the temperature control step includes causing a temperature of the positive characteristic sensitive element (A12-A16) to vary in the temperature variation pattern including a temperature rising period in which the temperature of the positive characteristic sensitive element (A12-A16) is raised within a temperature range equal to or higher than 20° C. and equal to or lower than 50° C. and a temperature falling period in which the temperature of the positive characteristic sensitive element (A12-A16) is lowered within the temperature range equal to or higher than 20° C. and equal to or lower than 50° C.

This aspect enables determining the air quality condition of a sample gas based on a variation pattern in the electrical characteristic value when the temperature of a positive characteristic sensitive element (A12-A16) is raised and lowered within the temperature range equal to or higher than 20° C. and equal to or lower than 50° C.

In an air quality determination system (1) according to a ninth aspect, which may be implemented in conjunction with the seventh or eighth aspect, the positive characteristic sensitive element (A12-A16) includes an organic composition (21) and conductive particles (22) dispersed in the organic composition (21). The positive characteristic sensitive element (A12-A16) includes at least one of first to fourth sensitive elements (A12-A16). The first sensitive element (A12) includes the organic composition (21) having siloxane on a main chain thereof and having no methyl group on a side chain thereof but having a polyethylene glycol group on the side chain thereof. The second sensitive element (A13) includes the organic composition (21) having polyethylene glycol on a main chain thereof and having no methyl group on a side chain thereof but having a nitro group on the side chain thereof. The third sensitive element (A14, A15) includes the organic composition (21) having siloxane on a main chain thereof and having no methyl group on a side chain thereof but having a cyano propyl group on the side chain thereof. The fourth sensitive element (A16) includes the organic composition (21) having siloxane on a main chain thereof and having no methyl group on a side chain thereof but having a cyano allyl group on the side chain thereof.

This aspect enables determining the air quality condition of a sample gas based on a variation pattern in the electrical characteristic value of a sensitive unit (2) including a positive characteristic sensitive element (A12-A16).

In an air quality determination method according to a tenth aspect, which may be implemented in conjunction with any one of the first to ninth aspects, the temperature control step includes controlling the temperature of the sensitive unit (2) by controlling a temperature control element (3) that heats and/or cools the sensitive unit (2). The temperature control element (3) includes at least one of a Peltier element or an electrothermal element.

This aspect enables causing the temperature of the sensitive unit (2) to vary in a temperature variation pattern using at least one of a Peltier element or an electrothermal element.

In an air quality determination method according to an eleventh aspect, which may be implemented in conjunction with any one of the first to tenth aspects, the acquisition step includes acquiring the electrical characteristic value of the sensitive unit (2) via a network.

This aspect allows the determination step to be performed by a determiner implemented on a cloud computing system.

An air quality determination method according to a twelfth aspect is a method for determining an air quality using a sensitive unit (2), of which an electrical characteristic value changes in reaction to one or more types of molecules. The air quality determination method includes a temperature control step, an acquisition step, a determination step, and an output step. The sensitive unit (2) includes a plurality of sensitive modules (2A-2F). The temperature control step includes controlling temperatures of the plurality of sensitive modules (2A-2F) exposed to a sample gas in a predetermined measurement period to cause the temperature of each of the plurality of sensitive modules (2A-2F) to vary in a temperature variation pattern including at least one temperature rising period in which the temperature of the sensitive module (2A-2F) rises and at least one temperature falling period in which the temperature of the sensitive module (2A-2F) falls. The acquisition step includes acquiring the electrical characteristic value of each of the plurality of sensitive modules (2A-2F) exposed to the sample gas. The determination step includes determining, using a learned model to determine an air quality condition of the sample gas, the air quality condition of the sample gas based on a variation in the electrical characteristic value of each of the plurality of sensitive modules (2A-2F). The output step includes outputting a decision made in the determination step.

This aspect enables reducing the chances of determining the air quality condition erroneously due to variation components caused by the temperature, thereby reducing the chances of causing a decline in the accuracy of the air quality condition determined. In addition, this aspect also enables determining, with respect to each of the plurality of sensitive modules (2A-2F), the air quality condition based on a variation in the electrical characteristic value acquired from each of the plurality of sensitive modules (2A-2F).

In an air quality determination method according to a thirteenth aspect, which may be implemented in conjunction with the twelfth aspect, each of the plurality of sensitive modules (2A-2C) includes: a plurality of sensitive elements (Ax) having mutually different sensitivities; and a board (20A-20F) on which the plurality of sensitive elements (Ax) are formed. Respective boards (20A-20F) of the plurality of sensitive modules (2A-2C) are mutually different boards.

According to this aspect, the boards (20A-20C) of the plurality of sensitive modules (2A-2C) are mutually different boards, thus allowing the respective temperatures of the plurality of sensitive modules (2A-2C) to vary in their desired temperature variation patterns.

In an air quality determination method according to a fourteenth aspect, which may be implemented in conjunction with the thirteenth aspect, each of the plurality of sensitive modules (2A-2C) includes the same combination of the plurality of sensitive elements (Ax) as any other one of the plurality of sensitive modules (2A-2C).

This aspect enables shortening, by overlapping, on the time axis, the respective measurement periods of the plurality of sensitive modules (2A-2C) with each other, the time interval at which the air quality condition is determined compared to a situation where the air quality condition is determined continuously with a single sensitive module.

In an air quality determination method according to a fifteenth aspect, which may be implemented in conjunction with the thirteenth aspect, each of the plurality of sensitive modules (2D-2F) includes a different combination of the plurality of sensitive elements from any other one of the plurality of sensitive modules (2D-2F).

This aspect enables determining the air quality for multiple different purposes by using a plurality of sensitive module(2D-2F) for the mutually different purposes.

In an air quality determination method according to a sixteenth aspect, which may be implemented in conjunction with the twelfth aspect, each of the plurality of sensitive modules (2A-2C) includes a plurality of sensitive elements (A1-A4) having mutually different sensitivities. The plurality of sensitive elements (A1-A4) included in each of the plurality of sensitive modules (2A-2C) are formed on a single board (20).

This aspect enables cutting down the number of parts required.

In an air quality determination method according to a seventeenth aspect, which may be implemented in conjunction with any one of the twelfth to sixteenth aspects, the plurality of sensitive modules (2A-2C) includes at least a first sensitive module and a second sensitive module. The temperature control step includes temporally shifting at least one of the temperature rising and falling periods of the first sensitive module from at least a corresponding one of the temperature rising and falling periods of the second sensitive module.

This aspect enables shortening, by temporally shifting at least one of the temperature rising and falling periods of the first sensitive module from that of the second sensitive module, the time interval at which the air quality condition is determined compared to a situation where the air quality condition is determined continuously with a single sensitive module.

An air quality determination system (1) according to an eighteenth aspect includes a sensitive unit (2), an exposure unit (10), a temperature control element (3), a controller (51), a determiner (55), and an outputter (56). An electrical characteristic value of the sensitive unit (2) changes in reaction to one or more types of molecules. The exposure unit (10) exposes the sensitive unit (2) to a sample gas in a predetermined measurement period. The temperature control element (3) heats and/or cools the sensitive unit (2). The controller (51) controls the temperature control element (3) to cause a temperature of the sensitive unit (2) exposed to the sample gas in the predetermined measurement period to vary in a temperature variation pattern including at least one temperature rising period in which the temperature of the sensitive unit (2) rises and at least one temperature falling period in which the temperature of the sensitive unit (2) falls. The acquirer (53) acquires the electrical characteristic value of the sensitive unit (2) in the predetermined measurement period. The determiner (55) determines, using a learned model (MD1) to determine an air quality condition of the sample gas, the air quality condition of the sample gas based on a variation in the electrical characteristic value. The outputter (56) outputs a decision made by the determiner (55).

According to this aspect, when the electrical characteristic value of the sensitive unit (2) changes in response to a molecule to which the sensitive unit (2) has sensitivity, the variation pattern of the electrical characteristic value in the temperature rising period and the temperature falling period changes from a variation pattern in a state where there are no molecules to which the sensitive unit (2) has sensitivity. This enables the determiner (55) to determine the air quality condition of the sample gas based on a variation in the electrical characteristic value in the temperature rising period and the temperature falling period. Consequently, this enables reducing the chances of determining the air quality condition erroneously due to variation components caused by the temperature, thereby reducing the chances of causing a decline in the accuracy of the air quality condition determined.

An air quality determination system (1) according to a nineteenth aspect includes a plurality of sensitive modules (2A-2C), an exposure unit (10), a temperature control element (3), a controller (51), a determiner (55), and an outputter (56). An electrical characteristic value of each of the plurality of sensitive modules (2A-2C) changes in reaction to one or more types of molecules. The exposure unit (10) exposes the plurality of sensitive modules (2A-2C) to a sample gas in a predetermined measurement period. The temperature control element (3) heats and/or cools the plurality of sensitive modules (2A-2C). The controller (51) controls the temperature control element (3) to cause the temperature of each of the plurality of sensitive modules (2A-2C) exposed to the sample gas in the predetermined measurement period to vary in a temperature variation pattern including at least one temperature rising period in which the temperature of the sensitive module (2A-2C) rises and at least one temperature falling period in which the temperature of the sensitive module (2A-2C) falls. The acquirer (53) acquires the electrical characteristic values of the plurality of sensitive modules (2A-2C) in the predetermined measurement period. The determiner (55) determines, using a learned model (MD1) to determine an air quality condition of the sample gas, the air quality condition of the sample gas based on variations in the electrical characteristic values of the plurality of sensitive modules (2A-2C). The outputter (56) outputs a decision made by the determiner (55).

This aspect reduces the chances of determining the air quality condition erroneously due to variation components caused by the temperature, thereby reducing the chances of causing a decline in the accuracy of the air quality condition determined. In addition, the determiner (55) may also determine, with respect to each of the plurality of sensitive modules (2A-2F), the air quality condition based on a variation in the electrical characteristic value acquired from each of the plurality of sensitive modules (2A-2F).

A sensor module (6) according to a twentieth aspect includes a sensitive unit (2) and a temperature control element (3). An electrical characteristic value of the sensitive unit (2) changes in reaction to one or more types of molecules. The temperature control element (3) heats and/or cools the sensitive unit (2). The temperature control element (3) causes a temperature of the sensitive unit (2) exposed to a sample gas in a predetermined measurement period to vary in a temperature variation pattern including at least one temperature rising period in which the temperature of the sensitive unit (2) rises and at least one temperature falling period in which the temperature of the sensitive unit (2) falls.

This aspect enables determining the air quality condition of a sample gas based on a variation in the electrical characteristic value in the temperature rising period and the temperature falling period, thus enabling reducing the chances of determining the air quality condition erroneously due to variation components caused by the temperature and thereby reducing the chances of causing a decline in the accuracy of the air quality condition determined.

Note that these are not the only aspects of the present disclosure but various configurations (including variations) of the air quality determination system (1) according to the exemplary embodiment described above may also be implemented as, for example, an air quality determination method, a (computer) program, or a non-transitory storage medium on which the program is stored.

Note that the features according to the second to twelfth aspects and the thirteenth to seventeenth aspects are not essential features for the air quality determination method but may be omitted as appropriate.

REFERENCE SIGNS LIST

1 Air Quality Determination System
2 Sensitive Unit
3 Temperature Control Element
10 Sensor Housing Chamber (Exposure Unit)
21 Organic Composition
22 Conductive Particle
51 Temperature Controller (Controller)
55 Determiner
Ax Sensitive Element
A1-A11 Negative Characteristic Sensitive Element
A12 Positive Characteristic Sensitive Element (First Sensitive Element)
A13 Positive Characteristic Sensitive Element (Second Sensitive Element)
A14, A15 Positive Characteristic Sensitive Element (Third Sensitive Element)
A16 Positive Characteristic Sensitive Element (Fourth Sensitive Element)
MD1 Learned Model

The invention claimed is:

1. An air quality determination method for determining an air quality using a sensitive unit, an electrical characteristic value of the sensitive unit changing in reaction to one or more types of molecules, the air quality determination method comprising:

a temperature control step including controlling a temperature of the sensitive unit exposed to a sample gas in a predetermined measurement period to cause the temperature of the sensitive unit to vary in a temperature variation pattern including at least one temperature rising period in which the temperature of the sensitive unit rises and at least one temperature falling period in which the temperature of the sensitive unit falls;

an acquisition step including acquiring the electrical characteristic value of the sensitive unit exposed to the sample gas;

a determination step including determining, using a learned model to determine an air quality condition of the sample gas, the air quality condition of the sample gas based on a variation in the electrical characteristic value; and an output step including outputting a decision made in the determination step, wherein the sensitive unit includes a negative characteristic sensitive element having a negative resistance coefficient in a temperature range equal to or higher than −20° C. and equal to or lower than 50° C., the negative characteristic sensitive element includes an organic composition and conductive particles dispersed in the organic composition, and the organic composition included in the negative characteristic sensitive element has siloxane on a main chain thereof and has a methyl group on a side chain thereof.

2. The air quality determination method of claim 1, wherein the determination step includes determining the air quality condition of the sample gas based on a difference between a first variation pattern and a second variation pattern, the first variation pattern being a variation pattern of the electrical characteristic value in a state where the temperature of the sensitive unit exposed to the sample gas is caused to vary in the temperature variation pattern, the second variation pattern being a variation pattern of the electrical characteristic value in a state where the temperature of the sensitive unit exposed to a standard gas is caused to vary in the temperature variation pattern.

3. The air quality determination method of claim 1, wherein the sensitive unit includes a plurality of sensitive elements having mutually different sensitivities, and the determination step includes determining the air quality condition of the sample gas based on respective variation patterns of the electrical characteristic value of the plurality of sensitive elements in a state where temperatures of the plurality of sensitive elements exposed to the sample gas are caused to vary in the temperature variation pattern.

4. The air quality determination method of claim 1, wherein the temperature control step includes causing a temperature of the negative characteristic sensitive element to vary in the temperature variation pattern including a temperature rising period in which the temperature of the negative characteristic sensitive element is raised within a temperature range equal to or higher than −20° C. and equal to or lower than 20° C. and a temperature falling period in which the temperature of the negative characteristic sensitive element is lowered within the temperature range equal to or higher than −20° C. and equal to or lower than 20° C.

5. The air quality determination method of claim 1, wherein the temperature control step includes controlling the temperature of the sensitive unit by controlling a temperature control element configured to heat and/or cool the sensitive unit, and the temperature control element includes at least one of a Peltier element or an electrothermal element.

6. The air quality determination method of claim 1, wherein the acquisition step includes acquiring the electrical characteristic value of the sensitive unit via a network.

7. The air quality determination method of claim 1, wherein the sensitive unit includes a plurality of sensitive modules, the temperature control step includes controlling temperatures of the plurality of sensitive modules exposed to the sample gas in the predetermined measurement period to cause the temperature of each of the plurality of sensitive modules to vary in the temperature variation pattern including the at least one temperature rising period and the at least one temperature falling period, the acquisition step includes acquiring the electrical characteristic value of each of the plurality of sensitive modules exposed to the sample gas, and the determination step includes determining, using the learned model, the air quality condition of the sample gas based on a variation in the electrical characteristic value of each of the plurality of sensitive modules.

8. The air quality determination method of claim 7, wherein each of the plurality of sensitive modules includes: a plurality of sensitive elements having mutually different sensitivities; and a board on which the plurality of sensitive elements are formed; and respective boards of the plurality of sensitive modules are mutually different boards.

9. The air quality determination method of claim 8, wherein each of the plurality of sensitive modules includes the same combination of the plurality of sensitive elements as any other one of the plurality of sensitive modules.

10. The air quality determination method of claim 8, wherein each of the plurality of sensitive modules includes a different combination of the plurality of sensitive elements from any other one of the plurality of sensitive modules.

11. The air quality determination method of claim 7, wherein each of the plurality of sensitive modules includes a plurality of sensitive elements having mutually different sensitivities, and the plurality of sensitive elements included in each of the plurality of sensitive modules are formed on a single board.

12. The air quality determination method of claim 7, wherein the plurality of sensitive modules includes at least a first sensitive module and a second sensitive module, and the temperature control step includes temporally shifting at least one of the temperature rising and falling periods of the first sensitive module from at least a corresponding one of the temperature rising and falling periods of the second sensitive module.

13. An air quality determination method for determining an air quality using a sensitive unit, an electrical characteristic value of the sensitive unit changing in reaction to one or more types of molecules, the air quality determination method comprising:

a temperature control step including controlling a temperature of the sensitive unit exposed to a sample gas in a predetermined measurement period to cause the temperature of the sensitive unit to vary in a temperature variation pattern including at least one temperature rising period in which the temperature of the sensitive unit rises and at least one temperature falling period in which the temperature of the sensitive unit falls;

an acquisition step including acquiring the electrical characteristic value of the sensitive unit exposed to the sample gas;

a determination step including determining, using a learned model to determine an air quality condition of the sample gas, the air quality condition of the sample gas based on a variation in the electrical characteristic value; and an output step including outputting a decision made in the determination step, wherein the sensitive unit includes a positive characteristic sensitive element having a positive resistance coefficient in a temperature range equal to or higher than −20° C. and equal to or lower than 50° C., the positive characteristic sensitive element includes an organic composition and conductive particles dispersed in the organic composition, and the positive characteristic sensitive element includes at least one of:

a first sensitive element including the organic composition having siloxane on a main chain thereof and having no methyl group on a side chain thereof but having a polyethylene glycol group on the side chain thereof;

a second sensitive element including the organic composition having polyethylene glycol on a main chain thereof and having no methyl group on a side chain thereof but having a nitro group on the side chain thereof;

a third sensitive element including the organic composition having siloxane on a main chain thereof and having no methyl group on a side chain thereof but having a cyano propyl group on the side chain thereof; or a fourth sensitive element including the organic composition having siloxane on a main chain thereof and having no methyl group on a side chain thereof but having a cyano allyl group on the side chain thereof.

14. The air quality determination method of claim 13, wherein the temperature control step includes causing a temperature of the positive characteristic sensitive element to vary in the temperature variation pattern including a temperature rising period in which the temperature of the positive characteristic sensitive element is raised within a temperature range equal to or higher than 20° C. and equal to or lower than 50° C. and a temperature falling period in which the temperature of the positive characteristic sensitive element is lowered within the temperature range equal to or higher than 20° C. and equal to or lower than 50° C.

15. A sensor module comprising:

a sensitive unit, an electrical characteristic value of the sensitive unit changing in reaction to one or more types of molecules; and a temperature control element configured to heat and/or cool the sensitive unit, the temperature control element being configured to cause a temperature of the sensitive unit exposed to a sample gas in a predetermined measurement period to vary in a temperature variation pattern including at least one temperature rising period in which the temperature of the sensitive unit rises and at least one temperature falling period in which the temperature of the sensitive unit falls, wherein the sensitive unit includes a negative characteristic sensitive element having a negative resistance coefficient in a temperature range equal to or higher than −20° C. and equal to or lower than 50° C., the negative characteristic sensitive element includes an organic composition and conductive particles dispersed in the organic composition, and the organic composition included in the negative characteristic sensitive element has siloxane on a main chain thereof and has a methyl group on a side chain thereof.

16. An air quality determination system comprising:

the sensor module of claim 15 which includes the sensitive unit and the temperature control element;

an exposure unit configured to expose the sensitive unit to the sample gas in the predetermined measurement period;

a controller configured to control the temperature control element to cause the temperature of the sensitive unit exposed to the sample gas in the predetermined measurement period to vary in the temperature variation pattern including the at least one temperature rising period in which the temperature of the sensitive unit rises and the at least one temperature falling period in which the temperature of the sensitive unit falls;

an acquirer configured to acquire the electrical characteristic value of the sensitive unit in the predetermined measurement period;

a determiner configured to determine, using a learned model to determine an air quality condition of the sample gas, the air quality condition of the sample gas being based on a variation in the electrical characteristic value; and an outputter configured to output a decision made by the determiner.

17. An air quality determination system comprising:

a plurality of sensor modules, each of the plurality of sensor modules being the sensor module of claim 15 and including the sensitive unit and the temperature control element;

an exposure unit configured to expose the sensitive unit of each of the plurality of sensor modules to the sample gas in the predetermined measurement period;

a controller configured to control the temperature control element of each of the plurality of sensor modules to cause a temperature of the sensitive unit of each of the plurality of sensor modules exposed to the sample gas in the predetermined measurement period to vary in a temperature variation pattern including at least one temperature rising period in which the temperature of the sensitive unit of each of the plurality of sensor modules rises and at least one temperature falling period in which the temperature of the sensitive unit of each of the plurality of sensor modules falls;

an acquirer configured to acquire the electrical characteristic values of the sensitive unit of each of the plurality of sensor modules in the predetermined measurement period;

a determiner configured to determine, using a learned model to determine an air quality condition of the sample gas, the air quality condition of the sample gas based on variations in the electrical characteristic values of the sensitive unit of each of the plurality of sensor modules; and an outputter configured to output a decision made by the determiner.

18. A sensor module comprising:

a sensitive unit, an electrical characteristic value of the sensitive unit changing in reaction to one or more types of molecules; and a temperature control element configured to heat and/or cool the sensitive unit, the temperature control element being configured to cause a temperature of the sensitive unit exposed to a sample gas in a predetermined measurement period to vary in a temperature variation pattern including at least one temperature rising period in which the temperature of the sensitive unit rises and at least one temperature falling period in which the temperature of the sensitive unit falls, wherein the sensitive unit includes a positive characteristic sensitive element having a positive resistance coefficient in a temperature range equal to or higher than −20° C. and equal to or lower than 50° C., the positive characteristic sensitive element includes an organic composition and conductive particles dispersed in the organic composition, and the positive characteristic sensitive element includes at least one of:

a first sensitive element including the organic composition having siloxane on a main chain thereof and having no methyl group on a side chain thereof but having a polyethylene glycol group on the side chain thereof;

a second sensitive element including the organic composition having polyethylene glycol on a main chain thereof and having no methyl group on a side chain thereof but having a nitro group on the side chain thereof;

a third sensitive element including the organic composition having siloxane on a main chain thereof and having no methyl group on a side chain thereof but having a cyano propyl group on the side chain thereof; or a fourth sensitive element including the organic composition having siloxane on a main chain thereof and having no methyl group on a side chain thereof but having a cyano allyl group on the side chain thereof.

19. An air quality determination system comprising:

the sensor module of claim 18 which includes the sensitive unit and the temperature control element;

an exposure unit configured to expose the sensitive unit to the sample gas in the predetermined measurement period;

a controller configured to control the temperature control element to cause a temperature of the sensitive unit exposed to the sample gas in the predetermined measurement period to vary in the temperature variation pattern including the at least one temperature rising period in which the temperature of the sensitive unit rises and the at least one temperature falling period in which the temperature of the sensitive unit falls;

an acquirer configured to acquire the electrical characteristic value of the sensitive unit in the predetermined measurement period;

a determiner configured to determine, using a learned model to determine an air quality condition of the sample gas, the air quality condition of the sample gas being based on a variation in the electrical characteristic value; and an outputter configured to output a decision made by the determiner.

20. An air quality determination system comprising:

a plurality of sensor modules, each of the plurality of sensor modules being the sensor module of claim 18 and including the sensitive unit and the temperature control element;

an exposure unit configured to expose the sensitive unit of each of the plurality of sensor modules to the sample gas in the predetermined measurement period;

a controller configured to control the temperature control element of each of the plurality of sensor modules to cause a temperature of the sensitive unit of each of the plurality of sensor modules exposed to the sample gas in the predetermined measurement period to vary in a temperature variation pattern including at least one temperature rising period in which the temperature of the sensitive unit of each of the plurality of sensor modules rises and at least one temperature falling period in which the temperature of the sensitive unit of each of the plurality of sensor modules falls;

an acquirer configured to acquire the electrical characteristic values of the sensitive unit of each of the plurality of sensor modules in the predetermined measurement period;

a determiner configured to determine, using a learned model to determine an air quality condition of the sample gas, the air quality condition of the sample gas being based on variations in the electrical characteristic values of the sensitive unit of each of the plurality of sensor modules; and an outputter configured to output a decision made by the determiner.

* * * * *